US008728478B2

(12) United States Patent
Saeed

(10) Patent No.: US 8,728,478 B2
(45) Date of Patent: May 20, 2014

(54) **IMMUNOGENIC *ESCHERICHIA COLI* HEAT STABLE ENTEROTOXIN**

(75) Inventor: A. Mahdi Saeed, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 13/054,983

(22) PCT Filed: Sep. 3, 2009

(86) PCT No.: PCT/US2009/004976
§ 371 (c)(1),
(2), (4) Date: Aug. 18, 2011

(87) PCT Pub. No.: WO2010/027473
PCT Pub. Date: Mar. 11, 2010

(65) Prior Publication Data
US 2011/0300185 A1  Dec. 8, 2011

Related U.S. Application Data

(60) Provisional application No. 61/093,975, filed on Sep. 3, 2008.

(51) Int. Cl.
*A61K 39/385* (2006.01)
(52) U.S. Cl.
USPC ............... 424/169.1; 424/400; 424/197.11; 530/389.5
(58) Field of Classification Search
None
See application file for complete search history.

(56) References Cited

U.S. PATENT DOCUMENTS

| 4,298,597 | A | * | 11/1981 | Acres et al. | 424/241.1 |
| 4,314,993 | A | * | 2/1982 | Wijnendaele | 424/197.11 |
| 4,411,888 | A | * | 10/1983 | Klipstein et al. | 424/194.1 |
| 4,499,080 | A | * | 2/1985 | Duflot et al. | 424/185.1 |
| 4,545,931 | A | * | 10/1985 | Houghten | 530/327 |
| 4,758,655 | A | * | 7/1988 | Houghten | 530/324 |
| 4,761,372 | A | * | 8/1988 | Maas et al. | 424/200.1 |
| 4,886,663 | A | * | 12/1989 | Houghten | 424/190.1 |
| 5,571,698 | A | * | 11/1996 | Ladner et al. | 435/69.7 |

(Continued)

FOREIGN PATENT DOCUMENTS

| EP | 1564286 A1 | 8/2005 |
| WO | WO 83/00018 | 6/1983 |

(Continued)

OTHER PUBLICATIONS

Brandwein, H. et al, Production of neutralizing monoclonal antibodies to *Escherichia coli* heat stable enterotoxin., Infection and Immunity, Jan. 1985, vol. 47(1), pp. 242-246, see materials and methods section.*

(Continued)

*Primary Examiner* — Albert Navarro
*Assistant Examiner* — Ginny Portner
(74) *Attorney, Agent, or Firm* — Schwegman, Lundberg & Woessner, P.A.

(57) ABSTRACT

The present invention relates to methods and compositions for the treatment and prevention of diarrhea and diarrheal related diseases and disorders in both animals and humans. In some embodiments, the invention relates to the treatment of said diarrhea and diarrheal related diseases and disorders with a vaccine. In still further embodiments, the invention relates to the treatment of constipation using the disclosed methods and compositions.

24 Claims, 37 Drawing Sheets

(56) References Cited

U.S. PATENT DOCUMENTS

| | | | | |
|---|---|---|---|---|
| 5,698,155 | A | | 12/1997 | Grosswald et al. ............ 264/402 |
| 5,853,978 | A | * | 12/1998 | Berman et al. ..................... 435/5 |
| 6,001,964 | A | * | 12/1999 | Gaynor et al. ................ 530/330 |
| 6,180,767 | B1 | * | 1/2001 | Wickstrom et al. .......... 536/22.1 |
| 7,118,879 | B2 | * | 10/2006 | Ladner et al. ...................... 435/9 |
| 7,527,802 | B2 | * | 5/2009 | Glenn et al. ............... 424/257.1 |
| 7,745,193 | B2 | | 6/2010 | Giannotta et al. |
| 7,776,338 | B2 | * | 8/2010 | Connell et al. ............. 424/190.1 |
| 2002/0076378 | A1 | * | 6/2002 | Wolfe et al. ..................... 424/9.4 |
| 2004/0121961 | A1 | * | 6/2004 | Masferrer ....................... 514/15 |
| 2004/0146534 | A1 | * | 7/2004 | Glenn et al. ............... 424/257.1 |
| 2006/0269477 | A1 | * | 11/2006 | Waldman ..................... 424/1.11 |
| 2007/0161040 | A1 | * | 7/2007 | Giannotta et al. ............. 435/7.1 |
| 2008/0095803 | A1 | | 4/2008 | Mekalanos |
| 2009/0017056 | A1 | * | 1/2009 | Tian et al. .................. 424/192.1 |
| 2009/0162315 | A1 | * | 6/2009 | Terman et al. ............... 424/85.2 |
| 2011/0077204 | A1 | * | 3/2011 | Kuchiiwa et al. ............ 514/17.7 |

FOREIGN PATENT DOCUMENTS

| | | | | |
|---|---|---|---|---|
| WO | 85/02611 | * | 6/1985 | |
| WO | WO 85 02611 | | 6/1985 | |
| WO | WO-02/064162 A2 | | 8/2002 | |
| WO | 02/070018 | * | 9/2002 | ............ A61K 47/48 |
| WO | 2006/007366 | * | 1/2006 | |
| WO | WO 2006/007366 | | 1/2006 | |

OTHER PUBLICATIONS

Kaufman, Peter E., Applied and Environmental Microbiology, Oct. 1981, vol. 42(4), pp. 611-614, Production and Evaluation of Antibody to Heat Stable Enterotoxin from a Human Strain of Enterotoxigenic *Escherichia coli*.*

Brandwein et al, 1985, Infection and Immunity, vol. 47(1), pp. 242-247, Production of neutralizing monoclonal antibodies to *Escherichia coli* heat stable enterotoxin, 1985.*

Alderete, John F et al, Infection and Immunity, Mar. 1978, vol. 19(3), pp. 1021-1030, Purification and chemical characterization of the Heat-Stable Enterotoxin Produced by Porcine strains of Enterotoxigentic *Escherichia coli*.*

Batisson, I et al, Infection and Immunity, Jul. 2000, vol. 68(7), pp. 4064-4074, Full Capacity of Recombinant *Escherichia coli* Heat Stable Enterotoxin fusion proteins for extracellular secretion, antigenicity, disulfide bond formation and Activity.*

Dreyfus, L.A. et al, Infection and Immunity, Nov. 1983, vol. 42(3), pp. 539-548, Chemical properties of Heat-stable Enterotoxins produced by Enterotoxigenic *Escherichia coli* of Different Host Origins.*

Fuentes, Manuel et al, Journal of Immunological Methods, vol. 307, pp. 144-149, 2005, Optimization of the modification of carrier proteins with aminated haptens.*

Aimoto, et al. "Amino-acid sequence of a heat-stable enterotoxin produced by human enterotoxigenic *Escherichia coli*" Eur J Biochem. 129(2):257-63 (1982).

Alderete, et al. "Purification and chemical characterization of the heat-stable enterotoxin produced by porcine strains of enterotoxigenic *Escherichia coli*." Infection and Immunity 19:1021-1030 (1978).

Arita, et al. "Purification and characterization of a new heat-stable enterotoxin produced by *Vibrio cholerae* non-O1 serogroup Hakata." Infect Immun. 59(6):2186-2188 (1991).

Carlson, et al. "Protein thiolation and reversible protein-protein conjugation. N-Succinimidyl 3-(2-pyridyldithio)propionate, a new heterobifunctional reagent." Biochemical Journal 173:723 (1978).

Clements, Construction of a nontoxic fusion peptide for immunization against *Escherichia coli* strains that produce heat-labile and heat-stable enterotoxins. Infection and Immunity 58:1159-1166 (1990).

Frantz, et al. "Immunological properties of *Escherichia coli* heat-stable enterotoxins: development of a radioimmunoassay specific for heat-stable enterotoxins with suckling mouse activity." Infection and Immunity 33:193-198 (1981).

Frantz, et al. "Investigation of synthetic *Escherichia coli* heat-stable enterotoxin as an immunogen for swine and cattle." Infection and Immunity 55:1077-1084 (1981).

Giannella, "Suckling mouse model for detection of heat-stable *Escherichia coli* enterotoxin: characteristics of the model." Infection and Immunity 14:95-99 (1976).

Giannella, "*E. coli* heat-stable enterotoxin and guanylyl cyclase C: new functions and unsuspected actions." Transactions of the American Clinical and Climatological Association 114:67-85 (2003).

Gounaris, et al. "Succinylation of pepsinogen." Journal of Biological Chemistry 242:2739-2745 (1976).

Gray, et al., "Peptide toxins from *Conus geographus* venom." The Journal of Biological Chemistry 256(10):4734-4740 (1981).

Guarino, et al., "*Citrobacter freundii* produces an 18-amino-acid heat-stable enterotoxin identical to the 18-amino-acid *Escherichia coli* heat-stable enterotoxin (ST Ia)." Infection and Immunity, 57(2):649-652 (1989).

Houghten, et al. "Chemical synthesis of an octadecapeptide with the biological and immunological properties of human heat-stable *Escherichia coli* enterotoxin." European Journal of Biochemistry 145:157-162 (1984).

Lateef, "An improved protocol for coupling synthetic peptides to carrier proteins for antibody production using DMF to solubilize peptides." Journal of Biomolecular Techniques 18:173-176 (2007).

Lowry, et al. "Protein measurement with the Folin phenol reagent." Journal of Biological Chemistry 193:265-275 (1951).

Molin, et al. "A new method for the study of glutaraldehyde-induced crosslinking properties in proteins with special reference to the reaction with amino groups." The Journal of Histochemistry and Cytochemistry 26:412-414 (1978).

Pereira, et al. "Antibody response against *Escherichia coli* heat-stable enterotoxin expressed as fusions to flagellin." Microbiology 147:861-867 (2001).

Saeed, et al. "Purification and characterization of heat-stable enterotoxin from bovine enterotoxigenic *Escherichia coli*." Infection and Immunity 40:701-710 (1983).

Saeed, et al. "Molecular homogeneity of heat-stable enterotoxins produced by bovine enterotoxigenic *Escherichia coli*." Infect Immun. 45(1):242-7 (1984).

Salvadori, et al. "Virulence factors of *Escherichia coli* isolated from calves with diarrhea in Brazil." Braz Journal of Microbiology 34:230-235 (2003).

Sanchez, et al. "Immunoactive chimeric ST-LT enterotoxins of *Escherichia coli* generated by in vitro gene fusion." FEBS Letters 208:194-198 (1988).

Savarino, et al., "Enteroaggregative *Escherichia coli* heat-stable enterotoxin 1 represents another subfamily of *E. coli* heat-stable toxin." Proc Natl Acad Sci U S A. 90(7):3093-7 (1993).

Sears, et al. "Enteric bacterial toxins: mechanisms of action and linkage to intestinal secretion." Microbiology Reviews 60:167-215 (1996).

Staples, et al. "Purification and Characterizationo f Heat-stable Enterotoxin Produced by a Strain of *E. coli* Pathogenic for Man." Journal of Biology Chemistry 155:4716-4721 (1980).

Takao, et al. "Amino acid sequence of a heat-stable enterotoxin isolated from enterotoxigenic *Escherichia coli* strain 18D." FEBS Lett. 152:1-5 (1983).

Takeda, et al. "Epitope mapping and characterization of antigenic determinants of heat-stable enterotoxin (STh) of enterotoxigenic *Escherichia coli* by using monoclonal antibodies." Infection and Immunity 61:289-294 (1993).

Wolf, "Occurrence, distribution, and associations of O and H serogroups, colonization factor antigens, and toxins of enterotoxigenic *Escherichia coli*." Clinical Microbiology Reviews 10:569-584 (1997); and.

Yoshitaki, et al. "Conjugation of Glucose Oxidase from *Aspergillus niger* and Rabbit Antibodies Using N-Hydroxysuccinimide Ester of N-(4-Carboxycyclohexylmethyl)-Maleimide." European Journal of Biochemistry 101:395 (1979).

Goldblatt, "Encyclopedia of Life Sciences." John Wiley and Sons, New York (2001), What pages?

Lefkovits, "Immunology Methods Manual." Harcourt Brace and Co., San Diego, Calif. (1997), What pages?

(56) References Cited

OTHER PUBLICATIONS

"The Merck Index." 12th ed., Merck & Co., Inc. (1996), what pages?

Physician's Desk Reference (62nd ed. 2008), what pages?

Kauffman, et al., "Production and Evaluation of Antibody to the Heat-Stable Enterotoxin from a Human Strain of Enterotoxigenic *Escherichia coli*." Appl Environ Microbiol. 42(4): 611-614 (1981)+.

Brandwein, "Production of neutralizing monoclonal antibodies to *Escherichia coli* heat stable Enterotoxin." Infection and Immunity, 1985, 47(1):242-246.

Flinn, et al. "A single-step method for the production of sugar hydrazides: intermediates for the chemoselective preparation of glycoconjugates." Bioconjug Chem. 16(3):722-8 (2005).

Hossany, et al. "Synthesis and immunochemical characterization of protein conjugates of carbohydrate and carbohydrate-mimetic peptides as experimental vaccines." Bioorg Med Chem. 12(13):3743-54 (2004).

Shin, et al. "Effective methods for the production of immunoglobulin Y using immunogens of *Bordetella bronchiseptica, Pasteurella multocida* and *Actinobacillus pleuropneumoniae*." J Vet Sci. 3(1):47-57 (2002).

Habeeb et al. (1958) "Molecular Structural Effects Produced in Proteins by Reaction With Succinic Anhydride," Biochemic. Biophysic. Acta, 29: 587-593.

Gianella (1976) "Suckling Mouse Model for Detection of Heat-Stable *Escherichia coli* Enterotoxin: Characteristics of the Model," Infection and Immunity, 14(1): 95-99.

Change et al. (1978) "Structural Studies on the Succinylated Bovine Serum Albumin," Int. J. Peptide Protein Res., 11:65-72.

Nasr-Eldin et al. (2011) "An Enhanced Protocol for Expression and Purification of Heat-Stable Enterotoxin of Enterotoxigenic *Escherichia coli*," J. Biochem. Molecular Toxicology, 26(4): 168-175.

"European Application Serial No. 09811838.3, Extended European Search Report mailed May 23, 2013", 10 pgs.

Aref, N.-E., et al., "An Enhanced Protocol for Expression and Purification of Heat Stable Enterotoxin of Enterotoxigenic *Escherichia coli*", J. Biochem. Molecular Toxicology, 26(4), (2012), 168-175.

Aref, N.-E., et al., "Design and characterization of highly immunogenic heat-stable enterotoxin of enterotoxigenic *Escherichia coli* K99+", Journal of Immunological Methods, 266, (2011), 100-105.

Aref, N.-E., et al., "Generation of high-titer of neutralizing polyclonal antibodies against heat-stable enterotoxin (STa) of enterotoxigenic *Escherichia coil*", Vaccine, 30, (2012), 6341-6346.

\* cited by examiner

FIGURE 2

Amide backbone      Side chains   binding site

Cys⁵-Cys⁶-Glu⁷-Leu⁸-Cys⁹-Cys¹⁰-Asn¹¹-Pro¹²-Ala¹³-Cys¹⁴-Ala¹⁵-Gly¹⁶-Cys¹⁷

(SEQ ID NO: 6)

1ˢᵗ β turn          2ⁿᵈ β turn        3ʳᵈ β turn

Crucial Structure of STa

STaP:    N-T-F-Y-C⁵-C⁶-E-L-C⁹-C¹⁰-N-P-A-C¹⁴-A-G-C¹⁷-Y (SEQ ID NO: 7)

STaH:    N-S-S-N-Y-C⁶-C⁷-E-L-C¹⁰-C¹¹-N-P-A-C¹⁵-T-G-C¹⁸-Y (SEQ ID NO: 8)

IgY MW = ~ 180 kD

IMMUNOGENIC *ESCHERICHIA COLI* HEAT STABLE ENTEROTOXIN

STATEMENT OF GOVERNMENT SUPPORT

This invention was made in part with government support under grant number N01-AI-30058, from the National Institutes of Health. As such, the United States government has certain rights to the invention.

FIELD OF THE INVENTION

The present invention relates to methods and compositions for the treatment and prevention of diarrhea and diarrheal related diseases and disorders in both animals and humans. In some embodiments, the invention relates to the treatment of said diarrhea and diarrheal related diseases and disorders with a vaccine. In still further embodiments, the invention relates to the treatment of constipation using the disclosed methods and compositions.

BACKGROUND OF THE INVENTION

Diarrheal diseases are one of the major causes of human death worldwide. Strains of enterotoxigenic *Escherichia coli* (ETEC) that produce heat-stable enterotoxin (STa) are an important cause of diarrheal disease in humans and animals. They are responsible for a significant proportion of diarrheal cases among infants, travelers going from non-endemic to endemic areas and neonatal mammals. The development of effective strategies to reduce the incidence and severity of ETEC-caused diarrhea has been hampered by the lack of an effective vaccine or immunotherapeutic agents against this enteric pathogen. Thus, there is a need to develop vaccines and other pharmaceuticals for the treatment of diarrhea and diarrheal related diseases and disorders.

SUMMARY OF THE INVENTION

The present invention relates to methods and compositions for the treatment and prevention of diarrhea and diarrheal related diseases and disorders in both animals and humans. In some embodiments, the invention relates to the treatment of said diarrhea and diarrheal related diseases and disorders with a vaccine. In still further embodiments, the invention relates to the treatment of constipation using the disclosed methods and compositions.

The present invention relates to methods and compositions of the enterotoxigenic *Escherichia coli* heat stable enterotoxin (STa) through its unique coupling to a modified protein carrier (such as a modified BSA or "MBSA") and its effective use to produce STa-specific neutralizing antibodies produced by animals immunized with the STa-conjugate (including but not limited to rabbits, cows, and egg laying chickens), for the treatment and prevention of diarrhea and diarrheal related diseases and disorders. In some embodiments, said composition further comprises at least one antibody or antibody fragment reactive with STa. In some embodiments, the invention relates to the treatment of said diarrhea and diarrheal related diseases and disorders by using the STa-MBSA conjugate as an immunizing vaccine of pregnant animals and women with the anticipation of the production of protective STa-specific antibody in the milk colostrums that will offer protection by passive immunization to the nursing newborn subject against diarrhea caused by the STa-producing *Escherichia coli*. In still further embodiments, the invention relates to the treatment of constipation and urinary retention in humans and animals using the STa-conjugate described under the disclosed methods and compositions. In additional embodiments, said vaccine is an injectable composition. In additional embodiments, said vaccine is a composition applied in patch form and the antigen is administered transdermally. In additional embodiments, said vaccine is used to prevent Traveler's diarrhea.

In some embodiments, the invention relates to a method for treating diarrhea or diarrheal related disease or disorder comprising: providing: a subject at risk for diarrhea or a diarrheal related disease or disorder, and a composition comprising a heat-stable enterotoxin from *Escherichia coli*, and administering said composition to said subject such that said symptoms are reduced. In further embodiments, said diarrhea or diarrheal related disease or disorder is selected from the group consisting of secretory diarrhea, osmotic diarrhea, motility-related diarrhea, inflammatory diarrhea, dysentery, infectious diarrhea, malabsorption disorders, inflammatory bowel syndrome, ischemic bowel disease, bowel cancer, hormone-secreting tumor related disorders, bile-salt diarrhea, chronic ethanol ingestion and urinary disorder. In still further embodiments, said subject is a mammal.

In some embodiments, the invention relates to a method for the prevention of diarrhea or diarrheal related disease or disorder in an unborn mammal comprising: providing: a subject impregnated with said unborn mammal, a composition comprising a heat-stable enterotoxin from *Escherichia coli*, and administering said composition to said subject such that the risk of said unborn mammal contracting said diarrhea or diarrheal related disease or disorder are reduced. In still further embodiments, said diarrhea or diarrheal related disease or disorder is selected from the group consisting of secretory diarrhea, osmotic diarrhea, motility-related diarrhea, inflammatory diarrhea, dysentery, infectious diarrhea, malabsorption disorders, inflammatory bowel syndrome, ischemic bowel disease, bowel cancer, hormone-secreting tumor related disorders, bile-salt diarrhea, chronic ethanol ingestion and urinary disorder. In additional embodiments, said subject is a mammal. In additional embodiments, said subject is a human.

In some embodiments, the invention relates to a method for treating constipation comprising: providing: a subject exhibiting symptoms associated with constipation that are resistant to common laxatives, and a composition comprising a heat-stable enterotoxin from *Escherichia coli*, and administering said composition to said subject such that said symptoms are reduced. In further embodiments, said subject is a mammal. In some embodiments, the invention relates to a vaccine comprising heat-stable enterotoxin protein from *Escherichia coli* comprising an amino terminus, a cross-linker comprising first and second ends, and a carrier protein, wherein said first end of said cross-linker is covalently attached to said amino terminus of said enterotoxin and said second end of said cross-linker is covalently attached to said carrier protein. In further embodiments, said carrier protein is bovine serum albumin. In still further embodiments, the ratio of enterotoxin molecules to one molecule of bovine serum albumin is between 1 and 35, preferably between 1 and 10, more preferably between 3 and 7 and even more preferably between 4 and 5. In further embodiments, said vaccine generates an antibody having a specific binding titer of at least $10^{-6}$. In further embodiments, said vaccine generates an antibody that has a neutralization capacity of at least $3 \times 10^4$ STa mouse units/ml. In additional embodiments, said enterotoxin protein has a specific activity of at least $1.22 \times 10^3$ MU/mg, more preferably at least $8.70 \times 10^3$ MU/mg and even more preferably $885 \times 10^4$ MU/mg. In further embodiments, said enterotoxin protein has a specific activity of at least. In still further embodiments, said vaccine is synthesized in the presence of a solvent. In additional embodiments, said solvent is dimethylformamide (DMF).

In some embodiments, the invention relates to a method of producing a STa-neutralizing antibody in egg laying hens, comprising: a) immunizing said hens with said Sta antigen; and b) collecting eggs, said eggs containing antibody reactive with said antigen. In some embodiments, the invention further relates to a method of producing a STa-neutralizing antibody in egg laying hens, comprising: a) immunizing said hens with said Sta antigen; and b) collecting eggs, said eggs containing antibody reactive with said antigen, wherein said antibody is extracted from the egg yolk of said eggs. In some embodiments, the invention relates to the previously mentioned STa-neutralizing antibody.

In some embodiments, the invention relates to a method for the treatment or prevention of diarrhea or a diarrheal related disorder comprising: administering said STa-neutralizing antibody to a subject. In some embodiments, the invention further relates to a method of administering said antibody wherein said STa-neutralizing antibody is an enterically coated antibody. In some embodiments, the invention further relates to an enterically coated STa-neutralizing antibody. In additional embodiments, said STa-neutralizing antibody is an injectable composition. In additional embodiments, said STa-neutralizing antibody is used to prevent Traveler's diarrhea.

BRIEF DESCRIPTION OF THE DRAWINGS

For a more complete understanding of the features and advantages of the present invention, reference is now made to the detailed description of the invention along with the accompanying figures.

FIG. 2 shows structural characteristics for particular amino acid sequences of *E. coli* heat-stable enterotoxin A (STa) (SEQ ID NO: 6). StaP, (SEQ ID NO: 7), refers to the porcine isolate of Sta, while StaH, (SEQ ID NO: 8), refers to the human isolate.

FIG. 3 shows the domain structures of guanylyl cyclases.

FIG. 4 shows one possible mechanism for the pathophysiology of *E. coli* diarrhea. It is not intended that the present invention be limited to any particular theory based upon said pathophysiology.

FIG. 5 shows the agarose electrophoresis gel of the PCR product of one embodiment of the present invention. Lane 1: 1500 bp ladder (DNA marker); Lane 2: Clinical *E. coli* isolate tested with 127 bp primer; Lane 3: Control *E. coli* strain (K12) tested with 127 bp primer; Lane 4: Clinical *E. coli* isolate tested with 244 bp primer; Lane 5: Control *E. coli* strain (K12) tested with 244 bp. Row A: 1500 bp ladder band; Row B: 500 bp ladder band; Row C: 100 bp ladder band.

FIG. 6 shows growth kinetic curves at various pH levels for ETEC on a 36 L batch ASM under different pH using a Bellco bioreactor.

FIG. 7 shows a revere-phase-high performance liquid chromatography elution profile of 60% HPLC-grade methanol-MCI gel-STa-rich fraction on a preparative C8 Vaydac separation column.

FIG. 8 shows the elution profile of biologically active *E. coli* heat-stable enterotoxin peaks on analytic Aquapore reverse-phase C8 Perkin-Elmer separation column.

FIG. 9 shows the matrix-assisted laser desorption ionization-time of flight (MALDI-TOF) mass spectroscopy profile of *E. coli* heat-stable enterotoxin.

FIG. 10 shows an illustration depicting the bovine serum albumin (BSA)-carrier protein-*E. coli* STa peptide conjugate.

FIG. 11 shows one possible mechanism for the reaction of succinic anhydride with the amino terminal group of a protein.

FIG. 12 shows a size exclusion chromatograph of a native and a succinylated BSA molecule.

FIG. 13 shows a MALDI-TOF mass spectrograph of a succinylated BSA molecule.

FIG. 14 shows a MALDI-TOF mass spectrograph of an *E. coli* enterotoxin peptide-succinylated BSA carrier conjugate.

FIG. 15 shows a MALDI-TOF mass spectrograph of an *E. coli* enterotoxin peptide-hypersuccinylated BSA carrier conjugate.

FIG. 16 shows a MALDI-TOF mass spectrograph calculation of the change in molecular weight and conjugation ratio of the *E. coli* heat-stable enterotoxin peptide-suBSA carrier conjugate.

FIG. 17 shows the procedure for performing an antibody capture ELISA assay as disclosed herein.

FIG. 18 shows *E. coli* STa-specific serum antibody neutralization bioassay: Group 1 (rabbits 1, 2 and 3). The straight horizontal line lies at 0.083 GW/RBW=Gut weight/remaining body weight ratio, signifying the cut off value for STa-positive SAM.

FIG. 19 shows the neutralization capacity of *E. coli* STa-specific serum antibody. The points represent the mean of neutralization titers from sera of three rabbits.

FIG. 20 shows an *E. coli* STa-specific serum antibody neutralization bioassay for all rabbits. Three rabbits showed STa neutralizing antibodies by 12 weeks, another 3 rabbits showed STa neutralizing antibodies by 17 weeks, and, 2 rabbits started to show STa neutralizing antibodies by 20 weeks post-immunization. GW=Gut weight; RBW=Remaining body weight.

FIG. 21 shows an *E. coli* STa-binding ELISA optimization screening serum dilution assay for optimal *E. coli* STa-STa antibody interaction.

FIG. 22 shows an *E. coli* STa-specific serum antibody: $10^{-4}$ serum dilution assay of group 1 rabbits.

FIG. 23 shows an *E. coli* STa-specific serum antibody: $10^{-4}$ serum dilution assay of group 2 rabbits.

FIG. 24 shows an *E. coli* STa-specific serum antibody: $10^{-4}$ serum dilution assay of group 3 rabbits.

FIG. 25 shows the mean O.D. value of group 1 rabbits after 20 weeks (post-immunization) at various serum dilutions.

FIG. 26 shows the mean O.D. value of group 2 rabbits after 20 weeks (post-immunization) at various serum dilutions.

FIG. 27 shows the mean O.D. value of group 3 rabbits after 20 weeks (post-immunization) at various serum dilutions.

FIG. 28 shows an end-titer of *E. coli* STa-specific serum antibody: 24 weeks (post-immunization) from eight rabbits.

FIG. 29 shows an *E. coli* STa-specific serum antibody end titer. The mean O.D. values of group 1, 2 and 3 rabbits after 24 weeks (post-immunization) at various serum dilutions are shown.

FIG. 30 shows a time-course evaluation of the avidity of *E. coli* STa-specific serum antibody using an ammonium thiocyanate dose response.

FIG. 31 shows a 5 M thiocyanate elution profile of *E. coli* STa-STa serum antibody complex. The mean O.D. of treated serum from rabbit groups 1, 2 and 3 is shown.

FIG. 32 shows an avidity index of *E. coli* STa-specific serum antibody from group 1, 2 and 3 rabbits using the avidity ELISA procedure disclosed herein.

FIG. 33 shows standardization and optimization of the process of egg yolk antibodies extraction and purification.

Figure 1:
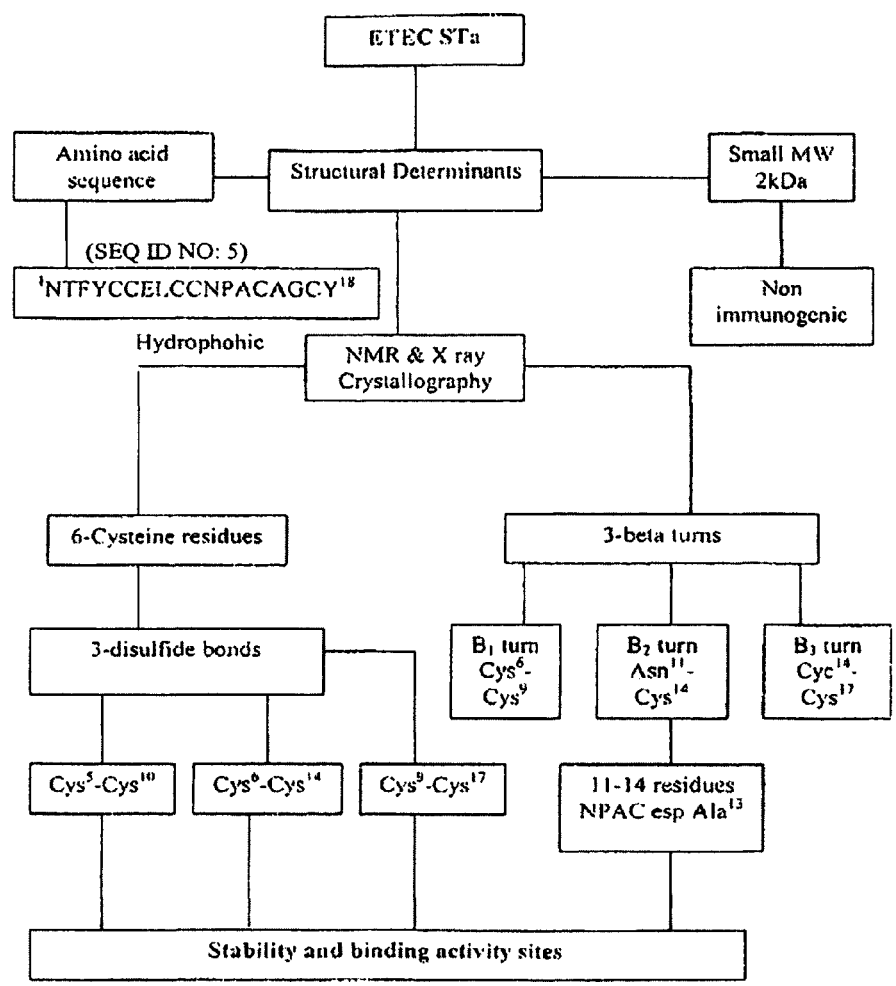
FIG. 1 shows the structural determinants of *Escherichia coli* heat-stable enterotoxin A (STa) (SEQ ID NO: 5).
Figure 3:
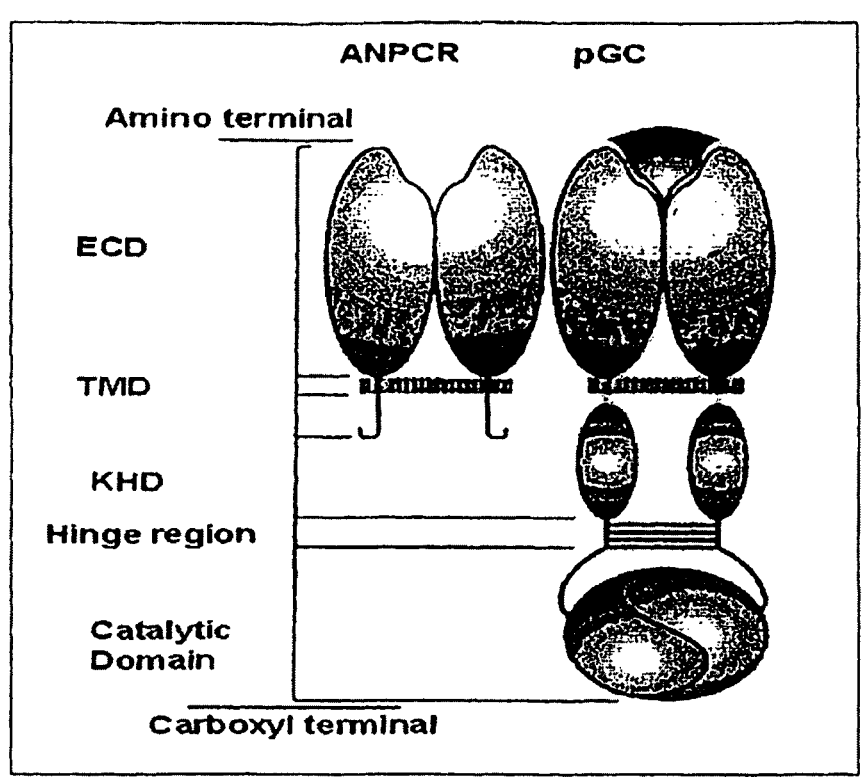
Figure 4:
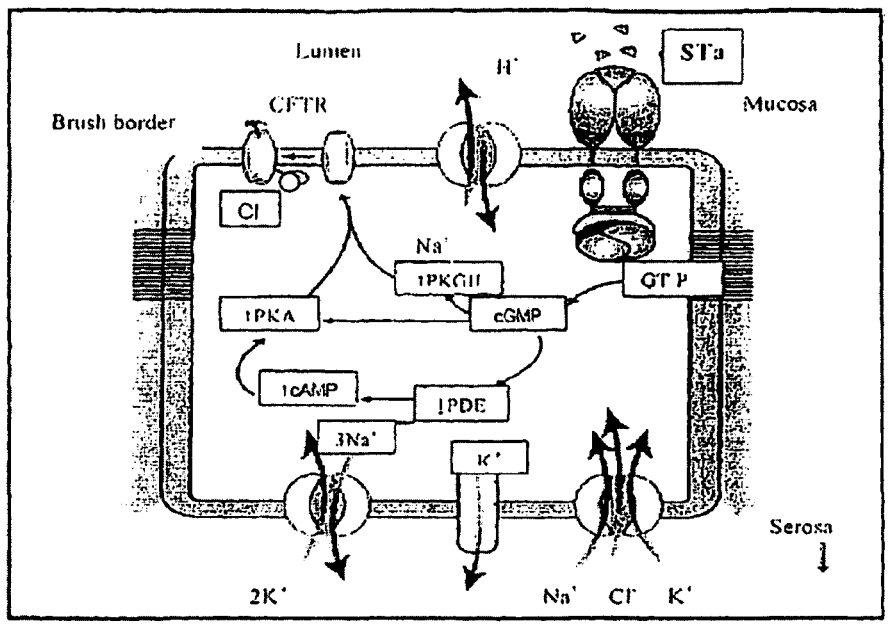

Table I shows several properties used to distinguish *E. coli* heat-stable enterotoxin A (STa) and heat-stable enterotoxin B (STb).

Table II shows amino acid quantity and sequence properties associated with various STa toxins (SEQ ID NOs: 9-19).

Table III shows the PCR primers used to detect the STa gene as described herein (SEQ ID NOs: 1-4).

Table IV shows the PCR running conditions for the detection of the STa gene as described herein.

Table V shows details of the PCR reaction for the detection of the STa gene as described herein.

Table VI shows the composition of the optimal minimal media for the production of STa (in g/L).

Table VII shows a summary of the purification procedures disclosed herein for *E. coli* STa per growth batch. MU=Mouse Unit=minimal amount of toxin producing intestinal weight to remaining body weight ratio≥0.085. Sp Ac=Specific activity=total mouse unit/protein concentration MED=Minimal effective dose=protein concentration per mg/total mouse unit per million. BAC=Batch absorption chromatography. Purification fold=specific activity of STa from each step/specific activity of STa in the cell free filtrate. Protein assay was done by Lowery method (Lowery, 1951) using a Perkin Elmer spectrophotometer.

Table VIII shows the results of the disclosed conjugation experiments, providing for the evaluation of the four disclosed conjugation protocols. DCC=N,N-dicyclohexyl carbodiimide; EDAC=1-ethyl-3-(3-dimethylaminopropyl)carbodiimide hydrochloride DMF=dimethylformamide; PB=Phosphate buffer. MES=2-(N-morpholino)ethanesulfonic acid buffer; suBSA=succinylated BSA. HS=hypersuccinylated BSA; P-NP=p-nitrophenol.

Table IX shows the amino acid compositional analysis of *E. coli* STa-su BSA carrier conjugate replicates.

Table X shows the approximate contribution of STa molecules to one molecule of modified BSA and a calculation of the conjugation ratio.

Table XI shows an *E. coli* STa-specific serum antibody end titer. The mean OD±SD value of group 1, 2 and 3 rabbits after 24-week post-immunization at various serum dilutions is shown.

Table XII shows Summary of STa-ELISA binding and neutralization end titers of rabbit sera immunized with STa-suBSA conjugate after the primary immunization and during the boosting intervals. The data were generated by STa-binding ELISA and STa-neutralization methods using a suckling mouse assay.

Table XIII shows a summary of the development of STa antibody avidity after multiple boosters with the STa conjugate using 5 M ammonium thiocyanate ELISA dissociation assay.

Table XIV shows Neutralization capacity of sera from animals immunized with several STa immuogens and the end titers of the STa-neutralizing antibodies.

Table XV show the neutralization capacity of STa-specific IgY extracted from egg yolk samples of 24 hens immunized with the STa vaccine. STa neutralization scores based on suckling mouse assay. A ratio of gut weight:remaining body weight of <0.085 signifies a positive STa-neutralization. Avidity index (%) for each sample is listed in the last column.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "diarrhea" and "diarrheal related diseases and disorders" refer to any condition that results in frequent loose or liquid bowel movements. While not limiting the scope of the present invention, diarrhea and diarrheal conditions may be incurred due to gastroenteritis, an inflammation of the gastrointestinal tract. Diarrhea and diarrheal related diseases and disorders include but are in no way limited to secretory diarrhea, osmotic diarrhea, motility-related diarrhea, inflammatory diarrhea, dysentery, infectious diarrhea, malabsorption disorders, inflammatory bowel syndrome, ischemic bowel disease, bowel cancer, hormone-secreting tumor related disorders, bile-salt diarrhea and chronic ethanol ingestion.

As used herein, "Sta" refers to the amino acid sequences of *E. coli* heat-stable enterotoxin A. StaP refers to the porcine isolate of Sta, while StaH refers to the human isolate.

A carrier protein is an antigenic polypeptide entity that induces the formation of antibodies directed against an antigen conjugated to it, by the immune system of an organism into which the carrier-antigen conjugate is introduced. Although many short epitopes are protective, they are poorly immunogenic. By conjugating an immunogenic carrier protein to a molecule that is poorly immunogenic, it is possible to confer higher immunogenicity. Such conjugate molecules stimulate the generation of an immune response and thus have been effectively used in vaccines that protect against pathogens for which protective immunity could not otherwise be generated.

Hence, highly immunogenic proteins (such as tetanus toxoid) have historically been used as carriers in order to induce a Th cell response that provides help to B cells for the production of antibodies directed against non-immunogenic epitopes. However, overall effectiveness has not been generally achieved with this approach, since the antibody response to a hapten (the epitope) coupled to a carrier protein can be inhibited when the recipient host has been previously immunised with the unmodified carrier protein. This phenomenon is termed epitope-specific suppression and has now been studied in a variety of hapten-carrier systems.

Useful antibodies or antibody fragments may be monoclonal or polyclonal. Antibodies may be made in birds. Mammalian antibodies are preferably of the class IgG, but may also be IgM, IgA, IgD or IgE. Fragments of an antibody, such as an Fab, Fv, CDR, etc. are contemplated.

Several immunologic carriers, some protein carriers, are known in the art, including, but not limited to, keyhole limpet hemocyanin (KLH), bovine serum albumin (BSA), ovalbumin (OVA), beta-galactosidase (B-GAL), penicillinase, poly-DL-alanyl-poly-L-lysine, and poly-L-lysine.

In one embodiment, the present invention contemplates modified carrier protein, such as modified BSA (MBSA). In one embodiment, the modified BSA is chemically modified, e.g. succinylated which results in "suBSA" succinylated BSA. In suBSA, Bovine serum albumin is modified with succinic anhydride so that lysine residues are acylated. The free amino groups are modified. The degree of modification can vary based upon how many amino groups are acylated. Succinic anhydride (SA) reacts rapidly with the E-amino groups of lysines and the a-amino groups of the N-termini of proteins at pH 7-9, forming an amide bond by replacing the amino group with a carboxyl. Thus, introducing a succinic anhydride moiety on BSA will afford a protein derivative with more carboxyl groups and hence increase the possibility to link STa from its amino terminal and preserve its antigenic determinants accosiated with the carboxyl terminal of the molecule. Hyper-Succinylated Bovine Serum Albumin (HS-BSA) is produced via an extensive modification of the BSA by introducing a large number of succinyl moieties [COO—] on the carrier protein could be achieved in to hyper-succinylation reaction.

As used herein, the terms "prevent" and "preventing" include the prevention of the recurrence, spread or onset of a disease or disorder. It is not intended that the present invention be limited to complete prevention. In some embodiments, the onset is delayed, or the severity of the disease or disorder is reduced. For example, in terms of severity, the number of bowel movements (and the consequent amount of water lost) is, in one embodiment, reduced. Alternatively, other symptoms, included but in no way limited to abdominal pain, fever, weight loss, dehydration, excessive perspiration, gastroenteritis, bloody stool and malabsorption of food may be reduced.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

"Subject" refers to any mammal, preferably a human patient, livestock, or domestic pet. A "subject at risk for diarrhea or diarrheal related disease or disorder" means a subject at risk for exposure to enterotoxigenic *Escherichia coli* (ETEC) and/or a subject residing or traveling in an area or areas afflicted by ETEC.

In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "vehicle" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

An enteric coating is a barrier applied to oral medication that controls the location in the digestive system where it is absorbed. "Enteric" refers to the small intestine, therefore enteric coatings prevent release of medication before it reaches the small intestine. Most enteric coatings work by presenting a surface that is stable at the highly acidic pH found in the stomach, but breaks down rapidly at a less acidic (relatively more basic) pH. For example, they will not dissolve in the acidic juices of the stomach (pH ~3), but they will in the higher pH (above pH 5.5) environment present in the small intestine. Materials used for enteric coatings include fatty acids, waxes, and shellac as well as plastics.

DETAILED DESCRIPTION OF THE INVENTION

The present invention relates to methods and compositions for the treatment and prevention of diarrhea and diarrheal related diseases and disorders in both animals and humans. In some embodiments, the invention relates to the treatment of said diarrhea and diarrheal related diseases and disorders with a vaccine. In still further embodiments, the invention relates to the treatment of constipation using the disclosed methods and compositions.

In some embodiments, the invention relates to the treatment of diarrheal disease and symptoms in mammalian subjects. Enterotoxigenic *Escherichia coli* (ETEC) is a major enteropathogen that causes potentially fatal diarrhea in both human and animal neonates as disclosed in Moon et al. (1993) *Vaccine* 11, 213-220 and Tacket et al. (1994) *Vaccine* 12, 1270-1274, both of which are incorporated by reference. It is also responsible for a large proportion of diarrheal disease among adult travelers as disclosed in Tacket et al. (1994) *Vaccine* 12, 1270-1274. Therefore, strategies to reduce the incidence and severity of ETEC diarrhea have been considered an important public health priority as disclosed in Tacket et al. (1994) *Vaccine* 12, 1270-1274. A large proportion of ETEC diarrhea is caused by heat-stable enterotoxin (STa), a small peptide (2kD), which is an important virulence determinant in enterotoxin-mediated diseases as disclosed in Sears et al. (1996) *Microbiology Reviews* 60, 167-215 and Giannella et al. (2003) *Transactions of the American Clinical and Climatological Association* 114, 67-85, both of which are hereby incorporated by reference. Upon infection, the STa-producing ETEC adheres to the epithelium of the small intestine via one or more colonization factor antigens or pili surface proteins. Once established, ETEC elaborates heat-stable enterotoxin (STa), which acts on a specific intestinal membrane bound receptor, guanylyl cyclase C, initiating a cascade of altered metabolic pathways. This may result in secretory diarrhea among affected adults and fatal dehydration in infants.

Methods for the treatment and control of ETEC diarrhea are still a matter of debate among veterinarians, livestock producers and other animal experts. The use of sub-therapeutic doses of antibiotics may help protect animals from some, but not all, diarrhea inducing bacterial strains. Moreover, the use of antimicrobials at sub-therapeutic levels has been linked to emerging antibiotic resistance among several bacterial species, including ETEC strains. While there are several reagents that are in use against ETEC derived diarrheal diseases in animals, most of these reagents are based on surface structures of the ETE strains. Furthermore, the development of a broad-spectrum vaccine against ETEC remains elusive as disclosed in Walker et al. (2007) *Vaccine* 25, 2545-2566, incorporated herein by reference. While not limiting the current invention to any particular theory, it is believed that two major technical problems contribute to this deficiency. The first involves the production of immunogenic preparations of antigens with the ability to confer broad-spectrum protection against ETEC infections. The second is the challenge of achieving effective mucosal immunization as disclosed in Walker et al. (2007) *Vaccine* 25, 2545-2566, due to the multiplicity, antigenic diversity, and high prevalence of unidentifiable forms of specific colonization antigens responsible for mucosal adherence as disclosed in Thomas et al. (1982) *Medical Microbiology and Immunology* 171, 85-90, incorporated herein by reference. Against this background, there is an urgent need to define a new common antigenic determinant that could provide broad protection against ETEC-STa-induced diarrhea. Saeed et al. (1985) *Microbiology and Therapy* 15, 221-229, hereby incorporated by reference, reported that calf scour could be experimentally induced by a highly purified STa preparation, supporting the notion that ETEC STa is the immediate mediator of diarrhea in claves. Additionally, several studies have demonstrated a significant correlation between STa-producing ETEC strains and diarrhea, and that 75% of ETEC strains produce STa either alone or in combination with heat-labile enterotoxin (LT) as provided for in Wolf (1997) *Clinical Microbiology Reviews* 10, 569-584, hereby incorporated by reference. Thus, the inclusion of STa in colonization factor-based ETEC vaccines or the production of neutralizing Sta antibodies would potentially offer immune protection against ETEC-caused diarrhea.

However, this approach has been a challenge, partly because of the haptenic nature of STa (molecular weight of less than 2 kDa), which fails to elicit an antibody response as provided for in Boedeker (2005) *Current Opinions in Gastroenterology* 21, 15-19, incorporated herein by reference. Additionally, the correlation between STa toxicity and antigenicity as disclosed in Takeda et al. (1993) *Infection and Immunity* 61, 289-294, hereby incorporated by reference, hampers the ability to produce a safe STa/CFAs vaccine. However, it was hypothesized that the poor immunogencity associated with the STa molecule could be improved by conjugation of the STa to a suitable macromolecule (carrier protein) as provided for in Pauillac et al. (1998) *Journal of Immunological Methods* 220, 105-114, incorporated herein by reference. While not limiting the scope of the present invention, it is believed that antibody-based therapy (passive immunization) targeting the STa antigen could be used to reduce the impact of ETEC-STa induced diarrhea and avoid the safety issue associated with active immunization with CFAltoxin based-vaccine. Attempts to conjugate the STa to a carrier protein have been disclosed in Clements (1990) *Infection and Immunity* 58, 1159-1166, incorporated herein by reference. However, previous disclosures were unclear regarding the efficiency and characteristics of these conjugates.

In preferred embodiments, the invention relates to a modified enterotoxin conjugate. The potential of using the vaccine to produce egg yolk-derived STa-antibody since it induced a very high titer of specific and neutralizing antibodies in immunized rabbits and recently in immunized egg laying hens at our laboratory (our recent data demonstrated that the STa conjugate induced a neutralizing antibody that we were able to extract from the yolk of eggs laid by the immunized hens).

In some embodiments, the invention relates to immunotherapy using antibodies raised against the conjugated STa toxin. In some embodiments, the invention relates to the using the STa-neutralizing antibodies as a prophylactic to prevent diarrhea. In some embodiments, the invention relates to the using the STa-neutralizing antibodies (or antibody fragments) to relieve symptoms of traveler's diarrhea and speed recovery. In some embodiments, the invention relates to the using the STa-neutralizing antibodies in a pill, powder, or injectible form.

In some embodiments, the invention relates to the using the STa-neutralizing antibodies as animal milk replacers additives and as additive to infant formula milk.

The potential of using this vaccine to immunize pregnant animals (cattle, sheep, goats, sows, horses and all animals that may be affected by the STa-producing *E. coli*). Immunization will produce STa-antibody enriched colostrums that will offer protection to newborn animals against diarrheal disease caused by STa-producing *E. coli*.

The potential of using the vaccine, and any of its modifications that may include changing the carrier to better suit human subjects, to immunize pregnant women to induce STa-antibody enriched colostrums that will protect the newborn infants against the STa-induced diarrheal disease (using subcutaneous, intramuscular, oral, skin patches, and inhalation routes).

The potential of using the vaccine to produce commercial amounts of STa-specific antibodies by immunizing dairy cattle and egg laying hens to extract and purify the antibodies from colostrums and eggs respectively using established technologies. These antibodies can be appropriately packaged and offered to humans (infants, children, adult travelers, and troops) and newborn animals (calves, piglets, sheep, and goats and other animals at risk of STa-induced diarrhea).

The potential of using the vaccine to treat human clinical disease such as: chronic constipation, urinary retention (after general anaesthesia), colon polyps and cancer, alleviate high blood pressure (hypertension) due to congestive heart failure and renal dysfunction, systemic dysfunctions including all enteric, glandular, neurological diseases that are mediated by disturbances in intracellular and particulate forms of cyclic GMP.

In some embodiments the invention relates to compositions of the enterotoxigenic *Escherichia coli* heat stable enterotoxin (STa) through its unique coupling to a modified protein carrier (such as a modified BSA or "MBSA") as a laxative. In some embodiments the invention relates to compositions of the enterotoxigenic *Escherichia coli* heat stable enterotoxin (STa) through its unique coupling to a modified protein carrier (such as a modified BSA or "MESA") as a laxative prior to colonoscopy or intestinal surgery. Conjugated STa could replace current magnesium laxatives, which are unpleasant to drink and must be taken well in advance of the procedure.

In some embodiments the invention relates to compositions of the enterotoxigenic *Escherichia coli* heat stable enterotoxin (STa) through its unique coupling to a modified protein carrier (such as a modified BSA or "MBSA") as a treatment of post-anaesthesia urine retention in humans, which would lower the need for post-operative catheterization.

In some embodiments the invention relates to compositions of the enterotoxigenic *Escherichia coli* heat stable enterotoxin (STa) through its unique coupling to a modified protein carrier (such as a modified BSA or "MBSA") in a Detection kits: using the antibodies to STa to make a detection kit for enteropathogenic *E. coli*.

Pharmaceutical Formulations

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155).

In a preferred embodiment, the active compound and optionally another therapeutic or prophylactic agent are formulated in accordance with routine procedures as pharmaceutical compositions adapted for intravenous administration to human beings. Typically, the active compounds for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for an orally administered of the active compound. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long acting, by dissolving or suspending the compound in oily or emulsified vehicles, which allow it to disperse only slowly in the serum.

Compositions for use in accordance with the present invention can be formulated in conventional manner using one or more physiologically acceptable vehicles or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosol (such as buccal, vaginal, rectal, sublingual) administration. In some embodiments, the administration is optical (e.g. eyes drops applied directly to the eye). In one embodiment, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol Syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

In addition to the formulations described previously, the compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference ($62^{nd}$ ed. 2008, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally another prophylactic or therapeutic agents are administered intramuscularly, intravenously, or subcutaneously. The active compound and optionally another prophylactic or therapeutic agent can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

In specific embodiments, it can be desirable to administer the active compound locally to the area in need of treatment. This can be achieved, for example, and not by way of limitation, by local infusion during surgery or topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

The amount of the active compound that is effective in the treatment or prevention of macular degeneration or angiogenesis can be determined by standard research techniques. For example, the dosage of the active compound which will be effective in the treatment or prevention of age-related macular degeneration can be determined by administering the active compound to an animal in a model such as, e.g., the animal models known to those skilled in the art. In addition, in vitro assays can optionally be employed to help identify optimal dosage ranges.

Selection of a particular effective dose can be determined (e.g., via clinical trials) by a skilled artisan based upon the consideration of several factors, which will be known to one skilled in the art. Such factors include the disease to be treated or prevented, the symptoms involved, the subject's body mass, the subject's immune status and other factors known by the skilled artisan.

The dose of the active compound to be administered to a subject, such as a human, is rather widely variable and can be subject to independent judgment. It is often practical to administer the daily dose of the active compound at various hours of the day. However, in any given case, the amount of the active compound administered will depend on such factors as the solubility of the active component, the formulation used, subject condition (such as weight), and/or the route of administration.

PREFERRED EMBODIMENTS

In a preferred embodiment, BSA was modified by introducing succinic moieties. Extensive modification of the free amino groups was achieved with the addition of succinic anhydride as disclosed in Habeeb (1967) *Journal of Immunology* 99, 1264-1276. The subsequent step in the design of STa-BSA conjugate was the cross-linking of STa to the modified BSA. In one embodiment, this reaction was initiated by incubation of the modified BSA with p-nitrophenol and DCC (i.e. a carbodiimide) for three hours to provide reactive ester groups that could easily attach the STa from its amino terminal, forming amide linkages. The use of DMF was shown to enhance the solubility of reactants including peptides and carrier proteins as disclosed in Lateef (2007) *Journal of Biomolecular Techniques* 18, 173-176, incorporated herein by reference. We believe that the use of DMF as a solvent reagent may have facilitated the solubility of the hydrophobic STa molecules, solving a problem encountered with the other solvents and coupling media. The STa-conjugate was tested for its protein content and biological activity. Based on the protein estimation, there was a conjugation efficiency of 52-64%. Moreover, this conjugate showed a higher biological activity than any activity reported in the previous STa-conjugates Experimental The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); C (degrees Centigrade); miR or miRNA (microRNA); BSA (bovine serum albumin); PCR (polymerase chain reaction); by (base pair).

Example I

Materials and Methods

Animals
  Swiss Webster Mice:
  A group of 20 Swiss-Webster (fifteen females and five males) was used to establish a colony as a source of suckling mice for STa bioassay. Exhausted females and males were continuously replaced with younger animals to ensure production efficiency of infant mice litters by the colony.
Reagents
  All reagents were obtained from commercial sources and were of analytical grade. Mobile phases used for purification of STa include HPLC-grade methanol, trifluoroacetic acid, as well as the other chemical ingredients listed under this section.

Verifying the ETEC K99+ Strain:

The PCR protocol disclosed in Olsvick et al. (1993) *Diagnostic Molecular Biology*, American Society for Microbiology (Washington, D.C.) and Salvadori et al. (2003) *Journal of Microbiology* 34, 230-235, both of which are hereby incorporated by reference, was used to detect the STa gene and verify the strain as STa-producing *E. coli*.

Bacterial Strains:

An ETEC strain was isolated from a clinically diarrheic neonatal calf and was provided by A. M. Saeed (Molecular Epidemiology Laboratory, National Food Safety Toxicology Center (NFST), Michigan State University (MSU), East Lansing, Mich.). A control strain (K-12 *E. coli*) was kindly obtained from the Bacterial Evolution Laboratory, NFST, MSU, East Lansing-Mich.

DNA Extraction (Template) by Boiling Lysis:

ETEC and K-12 strains were grown on Tripticase Soy Agar slants overnight at 37° C. A uniform bacterial colony from both strains was taken and suspended in 1 ml sterile Milli Qwater and boiled for 10 minutes, then left in ice for 5 minutes, followed by centrifugation at 13,000 rpm for 4 minutes. The supernatant was taken and kept at –20° C. until use as provided for in Holmes et al. (1981) *Analytical Biochemistry* 114, 193-197, hereby incorporated by reference.

Primer Selection and Preparation:

Two different sizes of STa primer, 244 bp and 127 bp (Table III), were obtained from Integrated DNA Technology Inc. (Coralville, Iowa). The STa primers for 244 base pair product (SEQ ID NO: 1) 5'-TCC GTG AAA CAA CAT GAC GG-3' and (SEQ ID NO: 2) 5'-ATA ACA TCC AGC ACA GGC AG-3'. The STI primers for 127 base pair product (SEQ ID NO: 3) 5'-TTA ATA GCA CCC GGT ACA AGC AGG-3' and (SEQ ID NO: 20) 5'-CTT GAC TCT TCA AAA GAG AAA ATT-3'. Both primers were prepared according to the manufacturer's instructions.

PCR Program:

PCR running conditions for detection of the STa gene is presented in Table IV using PCT-100 Programmable Thermal Controller (MJ Research, Inc). PCR reaction: The PCR reaction was performed as described in Table V using a Fisher exACTGene Complete PCR kit.

Agarose Gel Electrophoresis Analysis of PCR Products:

The analysis of the PCR products was performed in 2% agarose gel electrophoresis using the Horizontal Gel Electrophoresis System, Life Technology (Cat #11068-012). Briefly, two percent of agarose was prepared (1.5 gm/75 ml 1×TAE electrophoretic sequence grade) and ethidium bromide was added at a concentration of 3 µl/50 ml. The reagent was poured into the electrophoretic chamber and filled with 1×TAE. Five volumes of PCR product were mixed with 1 volume of gel loading buffer and loaded into the wells along with a 1.5 kb ladder. The agarose gel was left to run at the appropriate voltage (100-160 volts) for 30-45 minutes and examined via UV irradiation.

Purification and Characterization of *E. Coli* STa

STa was purified as disclosed in Staples et al. (1980) *Journal of Biology Chemistry* 155, 4716-4721, Saeed et al. (1983) *Infection and Immunity* 40, 701-710 and Saeed et al. (1985) *Analytical Biochemistry* 151, 431-437, all of which are hereby incorporated by reference.

Seed Culture and Frozen Stock of ETEC Preparation.

Casamino acid-yeast extract-salts (CAYE) seed culture was used for optimal growth of the ETEC strain as disclosed in Giannella (1976) *Transactions of the American Clinical and Climatological Association* 114, 67-85. The ETEC strain was grown on 500 ml of CAYE, incubated at 39° C. for 24 hours on a rotary shaker at 120 rpm, mixed with glycerol at a final concentration of 15%, then aliquoted into 10 ml samples and frozen at –80° C. (frozen stock).

Batch Medium (Asparagine Salt Medium) and Growth Conditions.

Medium was prepared as described in Staples et al. (1980) *Journal of Biology Chemistry* 155, 4716-4721. The disclosed media was found to offer several advantages, including high level of STa• production along with minimal contaminating proteins that facilitated the STa-purification process. Each batch consisted of 30 liters of culture-innoculated ASM grown in a 36 L omni vessel under different pH conditions (7.4, 8 and 8.6) using a Bellco bioreactor (Bellco Glass Inc., Vineland N.J.). Preculture was prepared by inoculating 10 ml of frozen stock of ETEC into IL of CAYE broth and was incubated at 39° C. for 24 hours on a rotary shaker at 120 rpm. The preculture medium was then transferred into 30 liters of batch medium and kept at 39° C. under continuous agitation at 120 rpm, aeration and oxygenation were at a rate of 5 Umin and 600 ml/min, respectively, through a sintered metal dispersion ring. Foam, speed of agitation, temperature and $O_2$ pressure was controlled using Bellco control modules. Samples were taken every two hours to determine the growth kinetics under various pH levels.

Preparation of Cell Free Filtrate.

After 24 hours of incubation, the growth medium was immediately filtered by tangential flow filtration through a 0.2 micron cassette in Millipore Pellicon System (Millipore Crop, Bedford, Mass.). Cell free filtrate was kept on ice throughout the time of filtration to minimize bacterial growth and enzymatic activity. Samples from the cell-free filtrate were collected for determination of total protein and STa content using suckling mouse assay.

Amberlite XAD-2 Batch Adsorption Chromatograph.

Cell-free filtrate was desalted and the hydrophobic STa was concentrated using Amberlite XAD-2 batch adsorption chromatography. Amberlite XAD-2 resin was first washed extensively with purified water to remove any preservative and powdery contaminants. Then 500 grams were suspended into 15 L of cell free filtrate in a 20 L carboy and kept overnight at 4° C. under gentle stirring. Resin was poured from the carboy into a 40 cm long glass column and washed with 5 L of Milli Qwater. The contaminants loosely bound to the resin were eluted with 1 L of 1% acetic acid in 20% methanol/water (v/v). A stepwise elution system was applied to elute the STa ~tarting with 1 L of 1% acetic acid in 80% methanol/water (v/v) followed by 1 L of 1% acetic acid in 99% methanol/water (v/v) and finally 1 L of 50% acetone/water (v/v). The last three fractions were pooled and concentrated by flash evaporation and freeze-drying. The resin was degassed for 5 minutes after each solvent was added to drain completely before further addition of solvent. Samples were collected for determination of the total protein and testing for STa biological activity in suckling mouse.

Acetone Fractionation.

Lyophilized crude STa was dissolved in 20 ml of 25% of acetic acid. Acetone was added to bring the final volume to 100-150 ml. After standing 1 hour at 4° C., the sample was centrifuged at 10,000 g for 30 minutes at 4° C. The supernatant fraction was evaporated to remove the acetone and was then freeze-dried. Samples were collected for protein determination and STa biological activity.

Reversed-Phase Batch Adsorption Chromatography (MCI-Gel).

An intermediate purification step was applied to the acetone STa-rich fraction to achieve a further level of STa purity. The lyophilized crude STa was solubilized in 100 ml of 0.1% of 20% HPLC-grade methanol. To this solution, 100 grams of Reverse-Phase Methacrylate Adsorbent Polymer Resin (340° A, 30 µm; Mitsubishi Chemical Corporation, Catalog #CHP2MGY-01 L) was slowly added under gentle mixing and the slurry was kept at 4° C. for 2 hours under gentle shaking. The slurry was poured into a 10-mm (inner diameter)×25-cm-long glass column. The column was washed with 300 ml 0.1% TFA/$H_2O$ (v/v). Stepwise elution of the proteins was performed with 100 ml of 0.1% TFA of 20, 40, 60, 80 and 100% MeOH (v/v). Fractions were collected separately from each elution step. The methanol and TFA were evaporated and the residues were tested for protein and STa biological activity.

Preparative Reverse-Phase High Performance Liquid Chromatography (RP-HPLC).

RP-HPLC was performed on Waters Associate Liquid Chromatography System equipped with multi-solvent delivery pumps, an automated gradient programmer 600S controller, Model 486 tunable absorbance detector using 7 µm, 300 Å, 25 cm×10 mm inner diameter Vydac C8 preparative columns (Sorbent Technologies, Inc., Atlanta, Ga.). Samples from RP-methacrylate adsorbent polymer resin were applied on an RP-C8 column and STa was eluted by gradient system with 0.1% TFA in water as solvent A and 0.1% TFA in 80% methanol as solvent B (0-30% for 5 min and 30-80% for 80 min). The UV absorbing peaks were detected at 214 nm. Peaks were collected separately and the methanol was evaporated then freeze-dried. The resulting freeze-dried substance was reconstituted into physiologically balanced saline and evaluated for protein content and STa biological activity.

STa Assessment for Biological Activity.

Detecting and quantifying STa biological activity was done using a reference standard in vivo model test, suckling mouse assay, according to Dean et al. (1972) *The Journal of Infectious Diseases* 125, 407-411 and Giannella (1976) *Infection and Immunity* 14, 95-99, both of which are hereby incorporated by reference. Newborn Swiss Albino suckling mice (2-3 days old) were randomly divided into groups (three each). Samples from RP-HPLC were serially diluted 1/100; 1/10, 000 & 100,000 and 10 µl of 0.2% Evans blue (w/v) was added per ml. Each suckling mouse was inoculated orally by 100-µl sample using a 1 ml syringe and a 20-µ-diameter polyethylene tube. Each sample dilution was tested in triplicate. After 2-hour incubation at room temperature, the mice were euthanized by carbon dioxide in a $CO_2$ chamber and the intestine, not including the stomach, was removed from each newborn mouse and weighed. The ratios of intestinal weight to remaining body weight of the three mice were determined. Animals with no dye in the intestine or with dye within the peritoneal cavity at autopsy were discarded. One unit of ST activity (one mouse unit) is defined as the minimal amount of toxin that produces an intestinal weight/carcass ratio of greater than 0.083.

Criteria for Homogeneity of Purified STa.

Homogeneity of the purified STa from preparative runs was validated by analytic aquapore RP-300A Perkin Elmer C8 column. Additionally, the exact molecular weight of STa was determined by matrix-assisted laser desorption ionization-time of flight mass spectroscopy (MALDI-TOF/MS). The purified STa was then submitted for amino acid sequencing.

Results and Discussion

Detection of STa Gene.

Figure 5:
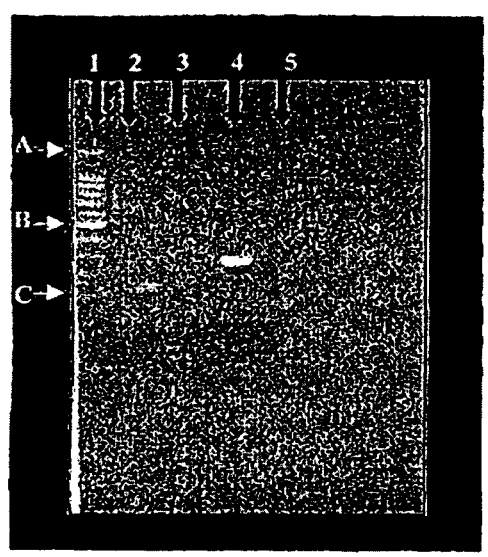

PCR amplification verified that the tested strain carried the gene encoding for STa after analyzing the product on gel electrophoresis. Two amplicon bands of 127 bp and 244 bp were detected under UV light for the tested strain, which were not apparent for the control strain (*E. coli* K-12) (FIG. 5).

Culture Analysis.

Figure 6:
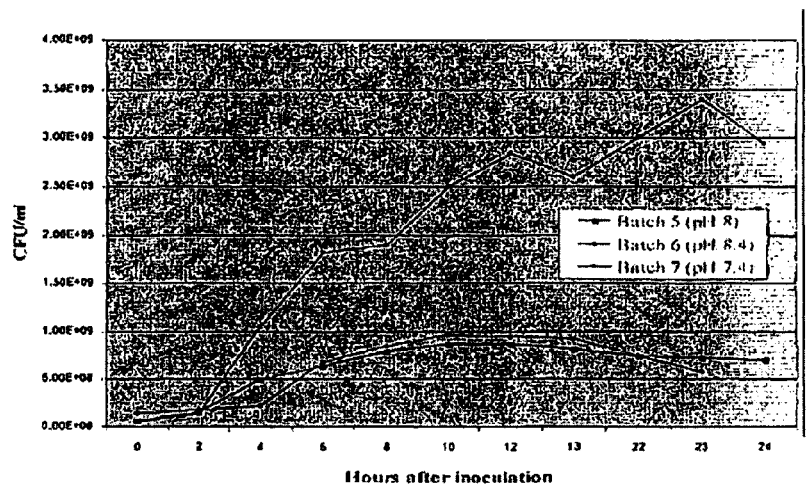

Growth kinetics experiments were conducted on 30 L batch cultures under various pH values (7.4, 8 and 8.5). Samples were taken every two hours and the growth pattern was determined by counting the total cell count (CFU/ml) using a robotic spiral plate and computer linked camera (Q counter). As FIG. 6 indicates, tested ETEC growth was maximal in medium in which the initial pH was adjusted to 7.4. This level of growth was associated with higher level of crude STa as verified by the suckling mouse assay.

Purification and Characterization of *E. coli* STa.

Table VII shows the summary of the purification scheme of SrTa for the ETEC *E. coli* in 30 L batch culture.

Amberlite XAD-2 Batch Adsorption Chromatography.

This step yields a high specific activity of the crude STa ($8.70 \times 10^3$ MU/mg protein) compared with the STa specific activity in the cell free filtrate ($1.22 \times 10^3$ MU/mg protein).

Acetone Fractionation.

Acetone fractionation resulted in further purification of the STa by removing additional amount of non-STa protein that was precipitated in acetone. Samples were taken for protein determination and STa biological activity. Specific activity of STa increased to $88.7 \times 10^3$ MU/mg protein.

Reversed Phase-Batch Adsorption Chromatography (MCI-Gel).

Specific activity of the STa at this step of purification increased from $88.7 \times 10^3$ to $112 \times 10^3$ MU/mg protein. This step allowed for a larger sample load on preparative RP-HPLC. Up to 15 mg of the crude STa cleaned by this procedure could be used as a single load in RP-HPLC without overloading the column or losing the resolution. This has led to a considerable reduction in the number of HPLC runs needed to purify STa.

Preparative Reverse-Phase HPLC Chromatography (RP-HPLC).

Figure 7:
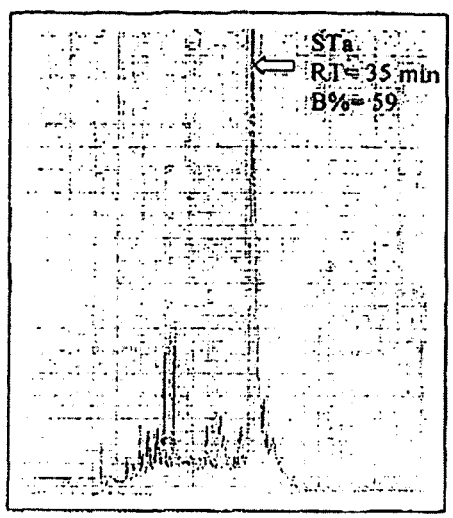
Figure 8:
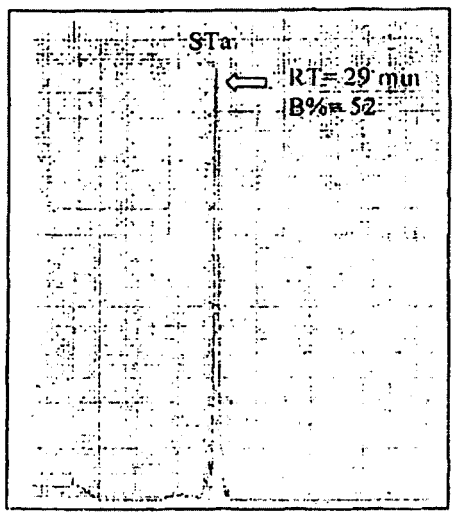

Sixty percent methanol MCI-gel STa-rich fractions were loaded on a preparative C8 column for further purification. FIG. 7 and FIG. 8 describe the elution profiles of STa. Elution with an increasing methanol gradient resulted in number of absorbance peaks at 214 nm (FIG. 7), the last of which was found to contain enterotoxin activity. The enterotoxin peak began to elute at approximately 55-60% methanol after 35 minutes retention time. This peak was collected and after methanol evaporation, was freeze-dried. It was then reconstituted into physiological saline and tested for STa biological activity and protein concentration. Further improvement in the STa specific activity ($885 \times 10^4$ MU/mg) was achieved in this step. The biological activity was demonstrated to be 0.113 ng per one mouse unit of STa minimal effective dose (MED) in 2-3 day-old inoculated Swiss Webster suckling mice.

Criteria for Homogeneity of Purified STa.

Analytic C8 Column:

Pooled peaks from several preparative RP-HPLC runs were tested on an analytic aquapore RP-300A Perkin Elmer C8 column to demonstrate a single symmetrical peak (FIG. 8).

Figure 9:
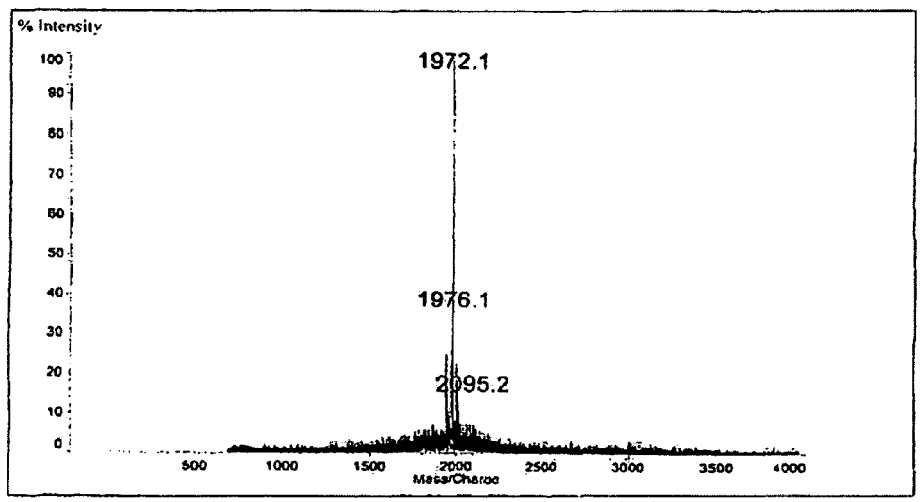
Figure 10:
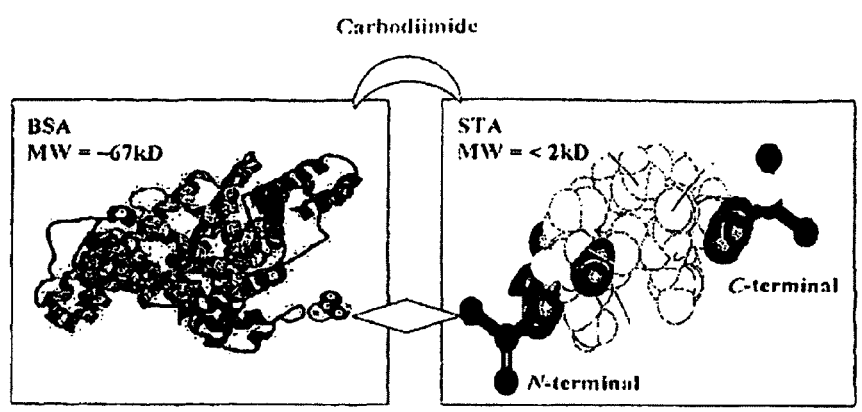

Mr-Value Determination Using Matrix Assisted Laser Desorption Ionization Time of Flight/Mass Spectroscopy:

A lyophilized HPLC-purified sample was analyzed by MALDI-TOF/MS to determine the molecular weight and the result is shown in FIG. 9. The observed signal at 100% MS intensity with mlc=1972.1 indicates that the $M_r$ of the purified product is 1972.1 Da, which is compatible with the $M_r$ (1969-1972) value calculated from amino acid composition of the STa, confirming the purity and identity of the purified product as the STa molecule. This was in agreement with the findings of Takao et al. (1983) *FEBS Lett.* 152, 1-5, incorporated herein by reference.

Amino Acid Sequence:

Further confirmation of the homogeneity and identity of the purified product was performed by determination of amino acid sequence. A lyophilized HPLC-purified sample was submitted for amino acid sequence analysis and the results showed the 18 amino acid residues of the STa molecule were matching the reported sequence.

Conclusions

This protocol includes concentrating the cell free filtrate using Amberlite XAD-2 batch adsorption chromatography (BAC), acetone fractionation, methacrylate polymer resin BAC and finally through RP-HPLC. Chemical analysis of the purified preparations matched the reported structure for this type of enterotoxin. The biological activity was demonstrated to be less than 0.2 ng per one mouse unit of the STa in 2-3 day-old inoculated Swiss Webster suckling mice. In summary, purification of STa to homogeneity was accomplished and the purity of the produced STa was documented through amino acid sequencing, and mass spectroscopy.

Example II

Methods and Materials

Reagents.

All reagents were obtained from commercial sources and were of analytical grade. Bovine serum albumin (BSA), succinic anhydride (SA), dioxane, N,N-dicyclohexylcarbodiimide (DCC), 1-ethyl-3-(3-dimethylaminopropyl carbodiimide hydrochloride (EDAC), N-methyl-imidazole, dimethyformamide (DMF), 2-(N-morpholino) ethanesulfonic acid buffer (MES), triethylamine ($ET_3N$), p-nitrophenol, sodium azide ($NaN_3$) and phosphate buffer saline (PBS) tablets were obtained from Sigma Chemical Co. (St. Louis, Mo.). STa was purified as described in Example I.

Procedure for Covalently Cross-Linking STa with Modified BSA:

Chemical modification of bovine serum albumin. Bovine serum albumin was chemically modified to introduce new carboxyl moieties using two different protocols:

Succinylation
Hyper-succinylation

Succinylation of Bovine Serum Albumin

Basis of Reaction.

Figure 11:
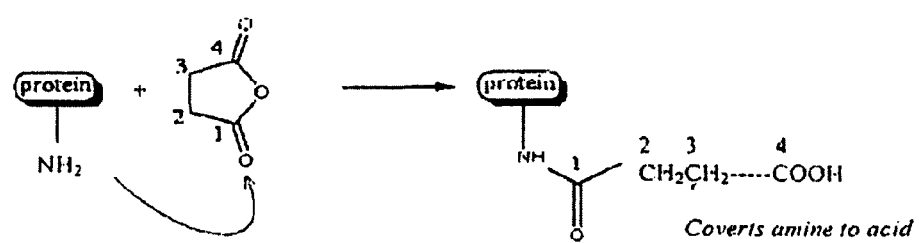

Succinic anhydride (SA) reacts rapidly with the E-amino groups of lysines and the a-amino groups of the N-termini of proteins at pH 7-9, forming an amide bond by replacing the amino group with a carboxyl as disclosed in Riordan et al. (1964) *Biochemistry* 11, 1768-1774, Gounaris et al. (1976) *Journal of Biological Chemistry* 242, 2739-2745 and *The Merck Index*, $12^{th}$ ed., Merck & Co., Inc. (1996), all of which are hereby incorporated by reference (FIG. 11). Thus, introducing a succinic anhydride moiety on BSA will afford a protein derivative with more carboxyl groups and hence increase the possibility to link STa from its amino terminal and preserve its antigenic determinants accosiated with the carboxyl terminal of the molecule.

Procedure:

The methods followed were those described by Habeeb (1967) *Biochemistry and Biophysics* 121, 652 and Habeeb (1967) *Journal of Immunology* 99, 1264-1276, both of which are incorporated herein by reference. Briefly, one gram of BSA was dissolved in 200 ml of 0.2 M borate buffer, pH 9.3. A 20 ml solution of dioxane with 5.4 g succinic anhydride was added in small aliquots over a period 30 minutes, the reaction mixture was stirred magnetically while maintaining the pH at 9.3 through the addition of 3 M NaOH. Following the last addition of succinic anhydride, the acylation reaction was allowed to continue for 45 minutes. The solution was then dialyzed at 4° C. against several changes of 0.01 M triethylamine using dialysis tubing with a M.W. cutoff of 12-14 KD. The dialyzed preparation was first freeze-dried and then further dried in a dessecator over phosphorous pentoxide ($P_2O_5$). Samples were taken and reconstituted in PBS buffer (pH 6.8) for size exclusion chromatography and mass spectroscopy.

Hyper-Succinylated Bovine Serum Albumin (HS-BSA)

Basis of Reaction.

An extensive modification of the BSA by introducing a large) number of succinyl moieties [COO—] on the carrier protein could be achieved in the hyper-succinylation reaction, The hyper-succinylation reaction was carried out in two steps, The first step involves the production of hyperaminated BSA by conversion of all free carboxyl groups on the BSA (aspartic and glutamic acids) into amino groups. The second step was the production of hypersuccinylated BSA by addition of succinic anhydride to the hyperaminated BSA to convert all amino groups (newly introduced, free, and N-terminal) into carboxyl groups.

Procedure:

Native BSA was treated with 1 mM of ethylenediamine at pH 4.75 in the presence of 10 mM EDAC. This hyperaminated protein molecule was then treated with 100 mmoles of succinic anhydride at pH 8.0 for two hours to produce a hyper-succinylated BSA molecule as disclosed in Fuentes et al. (2005) *Journal of Immunological Methods* 307, 144-149, incorporated herein by reference.

Coupling of *E. coli* STa to Modified BSA.

Four different conjugation protocols were used to covalently cross-linking STa to modified BSA. They were evaluated on the basis of stability of covalent bond, retained STa biological activity and the conjugation efficiency.

Protocol 1: Using Dimethylormamide (DMF) as a Solubilizer for the Peptide and Carrier Protein.

As described in Atassi (1981) *Biochimica et Biophysica Acta* 670, 300-330, incorporated herein by reference, DMF was used to solubilize several synthetic peptides before cross-linking them to carrier proteins. While not limiting the present invention to any particular theory, it is believed that this protocol enhances the coupling of the amino terminal ends of synthetic peptides to the carrier protein. In this study, the carrier protein (suBSA) was solubilized in DMF and then treated with p-nitrophenol to activate the carboxyl groups on the carrier.

Procedure:

Applying this procedure, we have used the purified native STa peptide and have solubilized it in DMF prior to addition to the modified suBSA. The mixture was kept stirring overnight at room temperature. This design encourages the STa coupling through its amino terminals based on nucleophilic attack at the reactive ester groups of the modified suBSA forming amide linkages. In a typical reaction, 140 mg of suBSA was suspended in 10 ml of anhydrous DMF and stirred it magnetically in a tight-capped foil-wrapped bottle for 3-4 hours. A solution of p-nitrophenol (65 mg/0.5 ml) in DMF was added and magnetic stirring continued for 15 minutes. A solution of DCC (50 mg/0.5 ml) was added to suBSA at a molar ratio of 120:1 and the reaction was allowed to continue stirring at room temperature for three hours. 100 mg of STa in 1 ml DMF was added to the activated suBSA at a molar ratio of 24:1. Shortly after, 1 ml of triethylamine was added. The reaction mixture was stirred overnight, at room temperature, while protected from direct light. The next day, 30 ml of Milli Q water was added and the mixture was dialyzed extensively against distilled water at 4° C. using a dialysis membrane with a 12-14 kD M.W. cutoff and then freeze-dried. Samples were taken for measurement of the STa biological activity of the conjugate using suckling mice assay (SMA), protein determination, biochemical and molecular characterization.

Protocol 2: Imidazole-Based Protocol.

The coupling procedure disclosed in Dean et al. (1990) *Journal of Immunological Methods* 129, 119-125, incorporated herein by reference, may be used to stabilize the carrier protein and minimize the formation of polymers due to the acylation process when the cross linker and the peptides intended for cross-linking are added.

Procedure:

0.5 M N-methyl-imidazole, pH 6.0, was used to dissolve the STa peptide and the carrier protein suBSA at a molar ratio (100:1). After the addition of EDAC (molar ratio: 50 mol EDAC/mol STa), the mixture was stirred for 30 minutes at room temperature followed by dialysis (M.W. cutoff: 12-14 kD) against distilled water at 4° C.

Protocol 3: Hyper-Succinylated BSA-Based Protocol.

Fuentes et al. (2005) *Journal of Immunological Methods* 307, 144-149, reported that an increase in the numbers of succinyl groups [COO—] on the carrier protein can enhance the cross linking of the peptides from their amino terminal. The procedure for hyper-succinylation of BSA was previously described herein.

Procedure:

In this coupling protocol, 3 mg hypersuccinylated-BSA was dissolved in 2.5 ml of 5 mM sodium phosphate buffer pH 7 and mixed with 2.5 ml of the STa peptide (0.5 mg/ml) in dioxane. EDAC was then added gradually to reach a concentration of 100 mM. After that, the conjugated composite was dialyzed using a tube with a M.W. cutoff 12-14 kD against distilled water at 4° C.

Protocol 4: Conventional Peptide-Carrier Coupling Protocol.

In this coupling procedure, suBSA, EDAC and MES buffer were used as disclosed in the EDC Conjugation Protocol Technical Sheet, *Uptima Interchim* (2007), incorporated herein by reference.

Procedure:

SuBSA carrier protein was dissolved in 0.1 M MES buffer, pH 5, to a final concentration of 10 mg/ml. Two milligrams of STa peptide were added to 2 mg of suBSA carrier protein. Then, EDAC (10 mg/ml in cold distilled water) was added at a ratio of 0.5 mg of EDAC per mg of total protein. The reaction was stirred for 2-3 hours at room temperature before dialysis at 4° C. against PBS using a tube of 12-14 kD molecular weight cutoff.

Dialysis.

The products of BSA modification and STa-modified BSA conjugation reactions were subjected to extensive dialysis to remove the small molecular weight reactants <<14 kD). Dialysis tubing with nominal M.W. cut-off 12-14 kD was purchased from Fisher Scientific (Pittsburgh, Pa.). STa-SuBSA conjugate was subjected to extensive dialysis against Milli Q purified water using a dialysis membrane of 12-14 kD M.W. cutoff. Molecular species of 14 kD or higher were retained inside the dialysis tube and all other reactants below 14 kD including uncoupled (free) toxin were dialyzed out.

Gel Filtration Chromatography (GFC).

PD-10 columns, Sephadex G-25M packed columns, of a nominal molecular mass exclusion limit of 5000 for protein were purchased from G.E. Healthcare (Buckinghamshire, UK). These columns are designed to separate proteins based on their molecular weight. The columns were equilibrated and developed by following the manufacturer's instructions. The dialyzed STa conjugate samples were passed through PD-10 Sephadex G-25 GFC column to purify the STa-suBSA conjugates from free STa, then assessed for biological activity and protein concentration. A freeze-dried STa-suBSA conjugate sample was reconstituted into 2.5 ml of PBS and passed through a PD-10 column to separate the unconjugated STa peptide from the portion that was successfully cross linked to the carrier protein. The STa-carrier conjugate was then eluted with 3.5 ml PBS and the effluent was collected and tested for biological activity in a suckling mouse assay.

Size-Exclusion High Performance Liquid Chromatography.

SE-HPLC was performed to compare the molecular size of both native and modified BSA. Bio-Sil® SEC-125 HPLC 300×7.8 mm filtration column (Catalog Number 125-0060) was purchased from BioRad (Hercules, Calif.) and hooked to the Waters Associate Liquid Chromatography System equipped with multi-solvent delivery pumps, an automated gradient programmer 600S controller and a tunable absorbance detector (Model 486). The column was equilibrated with 0.05 M sodium phosphate (dibasic), 0.05 M sodium phosphate (monobasic), 0.15 M NaCl and 0.01 M NaN) at pH 6.8. Isocratic elution system was applied at flow rate of 1 ml/min. The peak absorbance was monitored at UV wavelength of 280 nm.

Amino Acid Compositional Analysis.

To determine the conjugation ratio of STa to the modified BSA, a freeze-dried STa-suBSA conjugate sample was subjected to amino acid compositional analysis (Research Technology Support Facility (RTSF), Michigan State University).

Matrix-Assisted Laser Desorption Ionization/Time of Flight Mass Spectroscopy (MALDI-TOF/MS).

200 micrograms of freeze-dried STa-suBSA conjugate sample were subjected to MALDI-TOF/MS analysis at the MSU-RTSF laboratory to determine precisely the molecular weight of the conjugate and use this figure to calculate the number of STa molecules that covalently cross-linked to one BSA molecule (conjugation ratio).

Protein Assay.

Protein assays were performed according to the Lowery method as described in Lowry et al. (1951) *Journal of Biological Chemistry* 193, 265-275, incorporated herein by reference, using a Perkin Elmer Lambda 3A UV/US spectrophotometer.

STa-suBSA Conjugates Activity Bioassay.

The biological activity of the STa-suBSA conjugates was determined using the suckling mouse assay as described in Saeed et al. (1983) *Infection and Immunity* 40, 701, incorporated herein by reference.

Results

Table VIII shows the summary of conjugation experiments and their evaluation. More details on the DMF conjugation protocol are presented below.

Characteristics of the Modified BSA.

Figure 12:
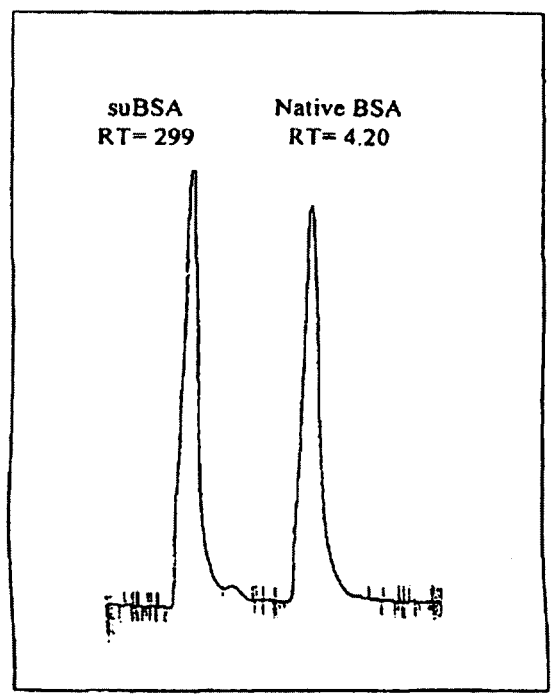
Figure 13:
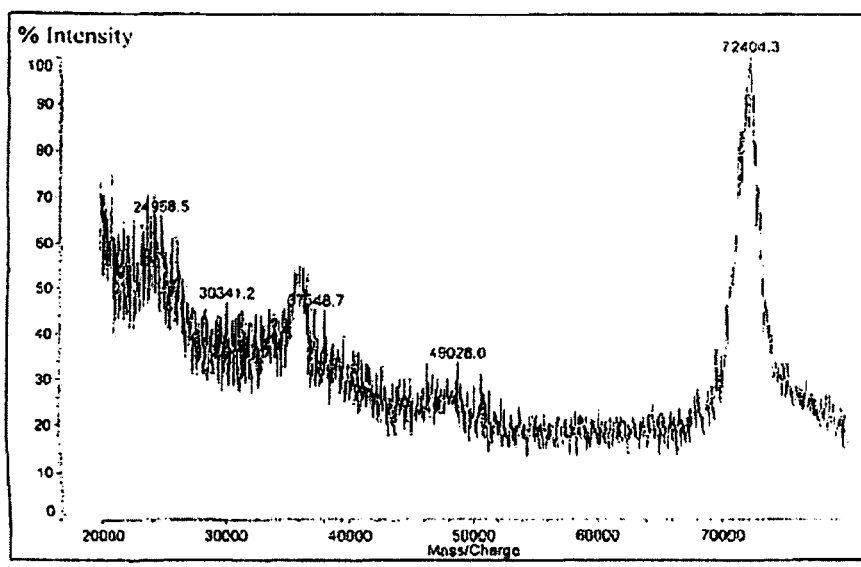

The results from SE-HPLC showed that modified BSA with succinic anhydride was eluted faster (RT=2.99 min) than native BSA (RT=4.20 min), suggesting that the molecular weight of suBSA had undergone a significance change (FIG. 12). Change in the molecular weight of the succinylated BSA was also confirmed by MALDI-TOF/MS. It was found that suBSA has a M.W. of 72.40 kD in comparison to native BSA which has a M.W. of ~67.00 kD (FIG. 13).

Characteristics of *E. coli* STa-suBSA Conjugates.

Dialysis and Gel Filtration Chromatography. A summary of the results is presented in Table VIII. The conjugation protocol based on the DMF method showed a higher rate of conjugation efficiency and higher level of retained STa biological activity compared to other conjugates (Table VIII). Further characterization of the DMF-based conjugation protocol is described below.

Amino Acid Compositional Analysis.

A dialyzed conjugate sample based on the DMF protocol was subjected to amino acid compositional analysis. Table IX shows the picomolar concentration and retention time of each amino acid residue.

Calculation of STa Peptide to SuBSA Ratio.

The conjugation ratio is defined as the number of STa molecules covalently cross-linked to one molecule of succinylated BSA. The amino acid composition of the conjugate was empirically determined by measuring the picomoles of each amino acid detected in a known volume of sample. Well-recovered residues, arginine and methionine, were used to quantify the concentration of each residue (pmole) in the conjugate sample. The number of STa molecules in the conjugate sample was calculated using the Arg and Meth residues not present within the sequence of the STa peptide. Table X gives the approximate number of coupled STa molecules to one molecule of modified BSA. Based on the data of amino acid compositional analysis, it was found that approximately 4-5 STa molecules were coupled to each molecule of suBSA.

STa Conjugate Analysis by MALDI-TOF/MS.

Figure 14:
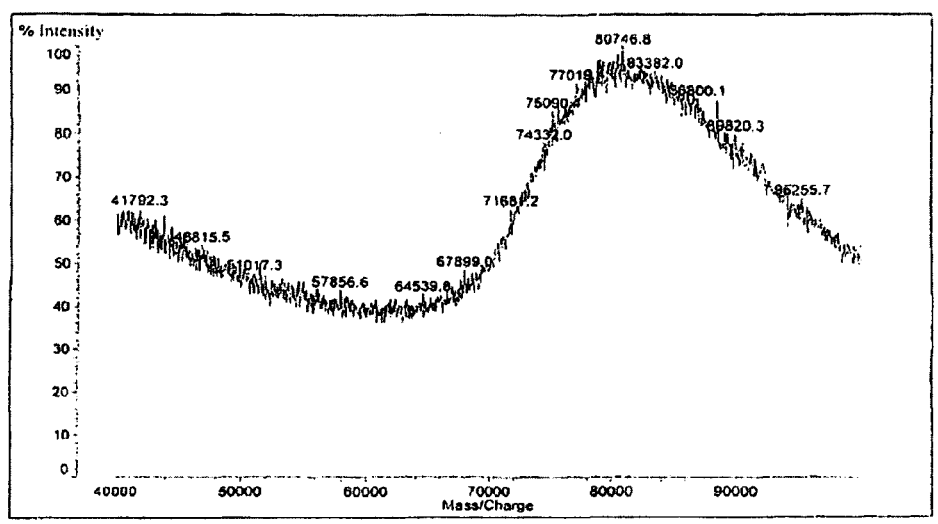
Figure 15:
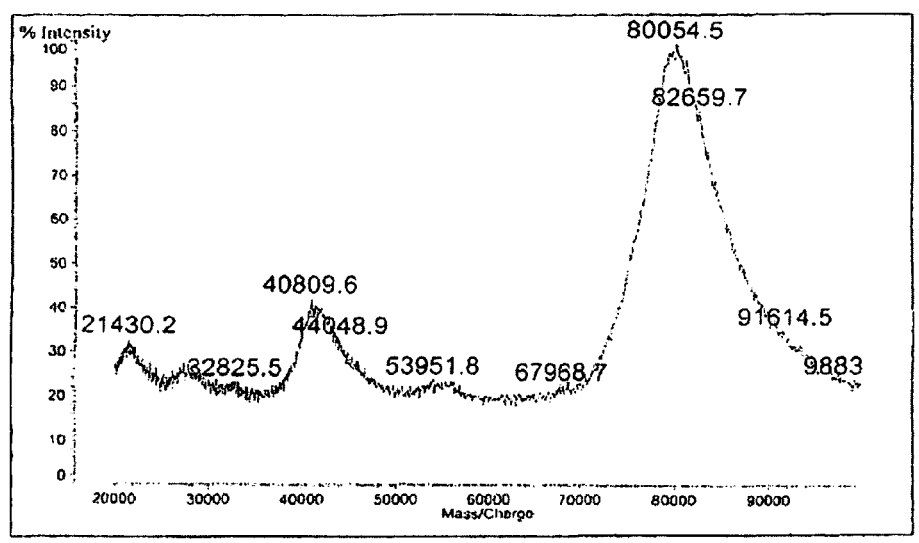
Figure 16:
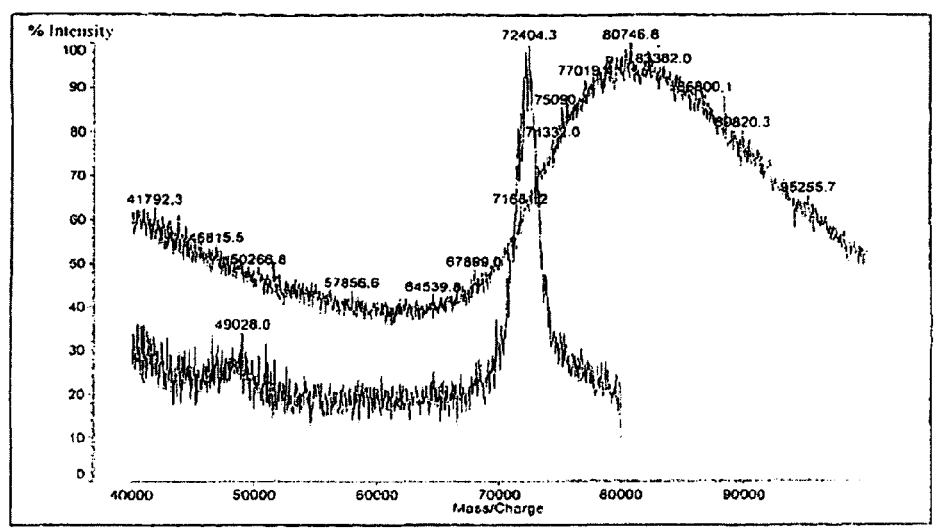
Figure 17:
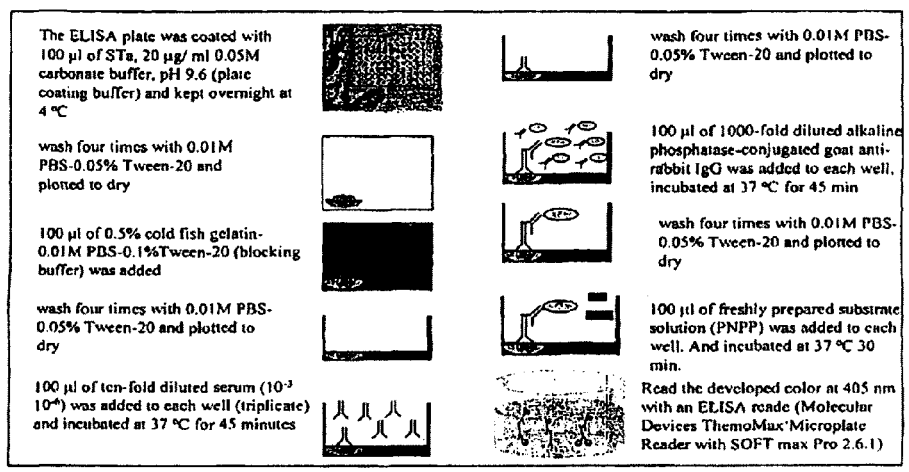

Lyophilized conjugate samples based on DMF and HS-BSA protocols were subjected to MALDI-TOF/MS to accurately determine the molecular weight ($M_r$ Value). Both samples showed median Mr Values over 80 kDa (FIG. 14 and FIG. 15). FIG. 16 shows the molecular weight differences for the modified BSA before and after STa peptide conjugation ($\Delta$M.W.=8342.5 Da). This difference was attributed to the contribution of the STa molecules. Based on this data, the median number of STa molecules successfully crossed linked to one molecule of suBSA was calculated from the following equation: $\Delta$M.W./STa M.W.=8342.5/1959=4–5. Four to five STa molecules were successfully crossed linked to one molecule of modified BSA based on DMF and HS-BSA protocols.

STa Conjugate Activity Bioassay and Conjugation Efficiency.

We concluded that the STa biological activity and the conjugation efficiency of the conjugate were highest in the DMF protocol. A summary of conjugation efficiency based on the tested protocols expressed largely by the conjugation ratios and the retained STa biological activities of the conjugates is presented in Table VIII.

Discussion

Numerous attempts have been made to render STa immunogenic, including chemical coupling and genetic fusions to appropriate carrier proteins as disclosed in Clements (1990) *Infection and Immunity* 58, 1159-1166, incorporated herein by reference. However, results of these studies showed limited success since the uncontrolled cross-linking process led to the loss of the biological activity of STa as a part of the conjugation process as disclosed in Pereira et al. (2001) *Microbiology* 147, 861-867. Additionally, these studies showed no sufficient details on the efficiency and the characteristics of the produced STa conjugates. The objective of this study was to design and characterize a well-defined, stable and active STa conjugate for further study of its immunogenicity in laboratory animal models. We have evaluated several conjugation protocols to achieve a stable biologically active STa conjugate through carefully planned cross-linking of the STa peptide to a modified carrier protein using BSA, carbodiimide derivatives and different solvents. Given the perceived molecular structure of the STa peptide and the desire to crosslink it through its amino terminus, we have selected carbodiimide coupling reagents. Other coupling reagents, glutaraldehyde and m-Maleimidobenzoyl-N-hydroxysuccinimide ester (MBS), may affect the 3-dimensional structure of the STa peptide. Glutaraldehyde binds non-specific amino groups and this leads to polymerization of peptide and/or carrier protein, which results in a poorly defined conjugate as disclosed in Molin et al. (1978) *The Journal of Histochemistry and Cytochemistry* 26, 412-414, incorporated herein by reference. Cysteine residues on the STa peptide play a crucial role in the biological activity and the stability of STa peptide. Thus, using MBS as a hetero-bifunctional reagent targeting thiol group on cysteine residue as disclosed in Carlson et al. (1978) *Biochemical Journal* 173, 723 and Yoshitaki et al. (1979) *European Journal of Biochemistry* 101, 395, both of which are incorporated by reference, may disrupt the disulfide bonds and affect the biological moieties on the STa peptide. BSA is widely used as a carrier protein in conjugation reactions because it is highly antigenic and can be easily modified to introduce a new moiety for specific coupling procedures as disclosed in Habeeb (1967) *Biochemistry and Biophysics* 121, 652 and Habeeb (1967) *Journal of Immunology* 99, 1264-1276. Therefore, the use of carbodiimide and BSA, in our conjugation reaction was justified based on a thorough understanding of the molecular structure of the STa peptide. In this study, BSA was modified by introducing succinic moieties, and its modification was confirmed using size exclusion chromatography and MALDI/TOF/MS. The data showed a 5000 Da difference in the molecular size between the modified and native BSA molecules, indicating an 8% increases in the M.W. of the modified BSA. This suggests that an extensive modification of the free amino groups was achieved with the addition of succinic anhydride as disclosed in Habeeb (1967) *Journal of Immunology* 99, 1264-1276. The subsequent step in the design of STa-BSA conjugate was the cross-linking of STa to the modified BSA. This reaction was initiated by incubation of the modified BSA with p-nitrophenol and DCC for three hours to provide reactive ester groups that could easily attach the STa from its amino terminal, forming amide linkages. The use of DMF was shown to enhance the solubility of reactants including peptides and carrier proteins as disclosed in Lateef (2007) *Journal of Biomolecular Techniques* 18, 173-176, incorporated herein by reference. We believe that the use of DMF as a solvent reagent may have facilitated the solubility. of the hydrophobic STa molecules, solving a problem encountered with the other solvents and coupling media. The STa-conjugate was tested for its protein content and biological activity. Based on the protein estimation, there was a conjugation efficiency of 52-64%, which is higher than previously disclosed in Frantz et al. (1981) *Infection and Immunity* 33, 193-198; Frantz et al. (1987) *Infection and Immunity* 55, 1077-1084 and Thompson et al. (1990) *Journal of Receptor Research* 10, 97-117, all of which are hereby incorporated by reference. Moreover, this conjugate showed a higher biological activity than any activity reported in the previous STa-conjugates (Table VIII). Based on these results, it is clear that most of the biological activity of the STa introduced into this reaction was retained in the conjugate even after extensive dialysis, GFC and SEC. Covalent attachment of STa molecules to modified BSA was documented by ammo acid composition analysis and MALDI-TOF/MS. A median value for the conjugation ratio of 4-5:1 STa:suBSA has been determined based on amino acid analysis and MALDI-TOF/MS (FIG. 16). Based on the results of the biological activity of this conjugate, we believe strongly that STa molecules may have been more efficiently oriented on the BSA carrier molecule via linkage through their amino terminals. Such orientation, achieved through the DMF protocol, has preserved the biologically active moiety of the STa and may offer an explanation for the relatively low yield of STa conjugate produced by other protocols in this study. The ineffective preservation and presentation of the STa biologically active moiety on previously studied STa conjugates may also explain the suboptimal immune response against STa in laboratory animals (Alderete et al. (1978) *Infection and Immunity* 19, 1021-1030; Lockwood et al. (1984) *Journal of Immunological Methods* 75, 295-307; Löwenadler et al. (1991) *FEMS Microbiology Letters* 82, 271-278 and Pereira et al. (2001) *Microbiology* 147, 861-867, all of which are hereby incorporated by reference.

In summary, we have designed a well-defined STa-conjugate based on a thorough understanding of the molecular structure of the STa peptide. After careful evaluation of several peptide-carrier conjugation protocols, we have defined the conditions for a conjugate that expressed a high STa biological activity in suckling mice. Its stability and biochemical attributes were characterized using GFC, amino acid analysis and MALDI-TOF/mass spectroscopy.

Example III

Methods and Materials

Reagents and Instruments.

STa-suBSA conjugates were designed and characterized as described above. All buffers ingredients, Freund's complete and incomplete adjuvant, alkaline phosphatase labeled goat-anti-rabbit IgG antibodies, p-nitrophenyl phosphate, fish gelatin, Tween-20 and ammonium thiocyanate (NH$_4$SCN) were obtained from Sigma Chemical (St. Louis, Mo.). Costar 3590 96-well microtiter plates were obtained from Fisher Scientific (Fairlawn, N.J.). Molecular Devices ThemoMax Microplate reader equipped with SOFT max Pro 2.6.1 was used to read the ELISA plate. A bleeding set (coagulant vacutainer tubes, adaptors and 20 gauge vacutainer needles) was obtained from Becton-Dickinson (BD) (Franklin Lakes, N.J.) and used for rabbit bleeding.

Animals.

Ten female New-Zealand albino rabbits (2-4 kg) were obtained from Charles River Laboratories (Wilmington, Mass.) and were housed in approved-size-single cages at the Containment Facility of Michigan State University. Temperature was kept at 20° C.±4° C., with 55% humidity. Rabbits were checked on a daily basis for their health status by qualified staff and veterinarians.

Immunization Procedure.

Standard operating procedures for handling and immunization of rabbits in compliance with the guidelines and recommendations for the Institutional Animal Care and Use Committee (lACUC) of Michigan State University were used. A water-in-oil emulsion of STa-conjugate in Freund's adjuvant was prepared as follows: 20 mg of freeze-dried STa-suBSA conjugate was reconstituted in 10 ml 0.01 M PBS-pH 7.0 and added to 10 ml of Freund's complete adjuvant (primary immunization). The mixture was homogenized with a polytron at 15,000 rpm for up to 10 minutes or until a stable water-in-oil emulsion was obtained. The ten rabbits were inoculated at multiple intradermal sites as disclosed in Vaitukaitis (1981) *Methods in Enzymology* 73, 46-52, incorporated herein by reference, with 0.5 ml of the described emulsion. Each rabbit was similarly inoculated with a booster dose at three-week intervals with 0.5 ml of STa conjugates mixed with Freund's incomplete adjuvant. Rabbits received boosters until STa-neutralizing antibodies titers were detected.

Animal Bleeding.

Pre-immunization blood samples were collected after one weak of adaptation from the central ear artery as provided for in Gordon (1981) *Journal of Immunological Methods* 44, 241-224, incorporated herein by reference, using serum separator BD-vacutainer tubes to obtain a reference baseline for serum titers. Blood samples were then collected three weeks after the primary immunization, approximately 4-5 days after each booster immunization. After collection, blood was allowed to clot for 60 min at 37° C. The clot was then separated from the sides of the collection vessel and allowed to contract at 4° C. overnight. The separated sera were collected by centrifugation at 2000 rpm for 30 min, aliquoted and kept at −20° C. The sera were tested for neutralization and binding capacity against STa using suckling mouse assay (SMA) and indirect ELISA binding assay respectively.

STa-Serum Neutralization Assay.

The STa-serum neutralization capacity was determined using the SMA as described by Frantz et al. (1987), hereby incorporated by reference. Briefly, three 50 µL aliquots of serum sample with were incubated with 25, 50 and 75 µL of STa (20 mouse units per µL) at 37° C. for 2 hours. The contents of each tube were brought to a final volume of 0.5 ml with PBS, before bioassay. Three mice were used for each sample. In addition, two controls were included; one has the 25 µL STa mixed with similar volumes of PBS instead of the tested sera and the second control had 25 µL STa mixed with similar volume of base line serum of the corresponding rabbit. All samples were treated similarly. Neutralization end titer of tested serum is defined as the highest serum dilution that neutralized one mouse unit of STa. Neutralization capacity is defined as the total mouse units of STa that were neutralized per one ml serum. Neutralization specific activity is defined as the total mouse units of STa that were neutralized per one mg serum protein.

Kinetics of the Rabbit Immune Response to ETEC STa Antibody-Capture ELISA for Screening Sera.

An indirect antibody-capture ELISA in which STa antigen was bound to a solid phase and reaction with antibody-containing samples was allowed (FIG. 20) in order to monitor the presence of STa antibodies in rabbit sera as described under the ELISA protocol as provided for in Lefkovits (1997) *Immunology Methods Manual*, Harcourt Brace and Co., San Diego, Calif., incorporated herein by reference. The ELISA plates were coated with 2.5 ~g STa and 100 µL of 0.05 M carbonate buffer, pH 9.6, (plate coating buffer) and incubated overnight at 4° C. Plates were washed four times with 0.01 M PBS-0.05% Tween-20 and blotted dry. 100 µL of 0.5% cold fish gelatin-0.01% M PBS-0.1% Tween-20 (blocking buffer) was added to each well to block nonspecific binding sites on the plastic surface and incubated at 37° C. for 30 minutes. Plates were then washed with 0.01 M PBS-0.1% Tween-20

(washing buffer) and blotted. Serum samples collected from all rabbits over the period of immunization were screened at a ten-fold dilution with PBS-0.1% Tween-20. 100 μL of each serum dilution ($10^{-3}$, $10^{-4}$, $10^{-5}$ and $10^{-6}$) was added to each well, in triplicate, and incubated at 37° C. for 45 minutes. After four washings and blotting, 100 μL of 1000-fold diluted alkaline phosphatase-conjugated goat anti-rabbit IgG antibodies (1 μL/ml) was added to each well, incubated at 37° C. for 45 minutes. Plates were washed as previously described and 100 μL of freshly prepared substrate solution (one tablet set of p-nitrophenyl phosphate (pNPP/PBS)/5 ml in 0.1 M diethanolamine buffer, pH 9.8) was added to each well. The reaction was allowed to develop for 30 minutes at 37° C. The developed color was read at 405 nm with an ELISA plate reader (Molecular Devices "ThemoMax" Microplate Reader with SOFT Max Pro 2.6.1). Reciprocal value of the maximal dilution of serum that had a mean plus 2 standard deviations (x+2 SO) O.D. value or higher than the O.D. of the baseline serum sample, was reported as antibody end titer for each tested serum sample.

Avidity ELISA.

Avidity (Functional Affinity) is the measure of the overall strength of interaction of an antigen with many antigenic determinants with multivalent antibodies as provided for in Goldblatt (2001) *Encyclopedia of Life Sciences*, John Wiley and Sons, New York, incorporated herein by reference. In this study, the STa-antibody avidity was measured by comparing the amount of antibodies that could bind the STa antigen in the presence or absence of increasing concentrations of a chaotropic agent. In this test, a mild chaotropic agents, ammonium thiocyanate" was added in increasing molar concentrations to the antibody-antigen mixture. Antibodies of low avidity are more likely to dissociate from antigen-antibody complexes than those of higher avidity as described by Ferreira et al. (1995) *Journal of Immunological Methods* 187, 297-305, incorporated herein by reference.

The procedure was performed using similar steps to the ELISA protocol described above. However, after the final incubation of the tested sera, four washings and blotting, 100 μL of three different molar concentrations of ammonium thiocyanate in PBS (5 M, 2.5 M, and 1.25 M) were added to each well, in duplicates, incubated at 37° C. for 15 minutes. Plates were processed then as described under the ELISA protocol. Avidity index was calculated as a percentage of the O.D. of the sample with different concentrations of ammonium thiocyanate and the O.D. of the sample without treatment. Serum samples obtained from rabbits before the initial immunization were used as baseline controls.

Statistical Analysis.

Generated ELISA O.D. data were adjusted and subjected to statistical analysis for the calculation of the mean and standard deviation. ELISA O.D. data was plotted using Microsoft Excel.

Results

Characterization of Serum Antibody Response in STa-Conjugate-Immunized Rabbits.

Figure 18:
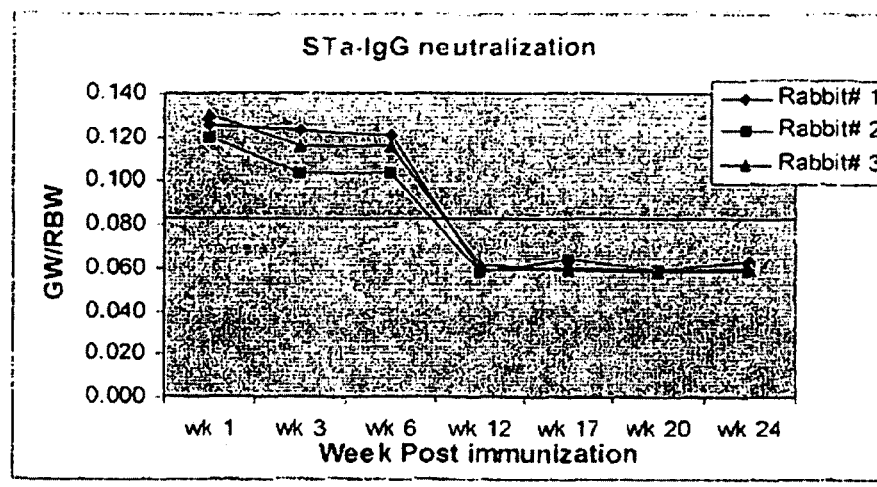
Figure 19:
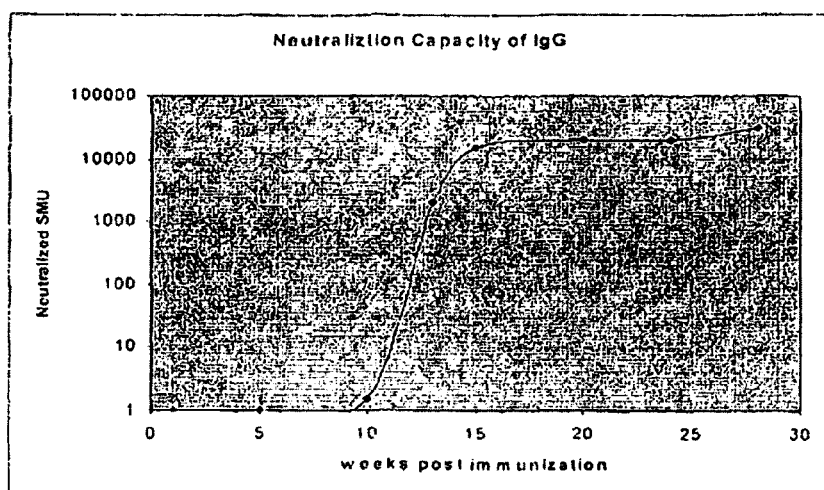
Figure 20:
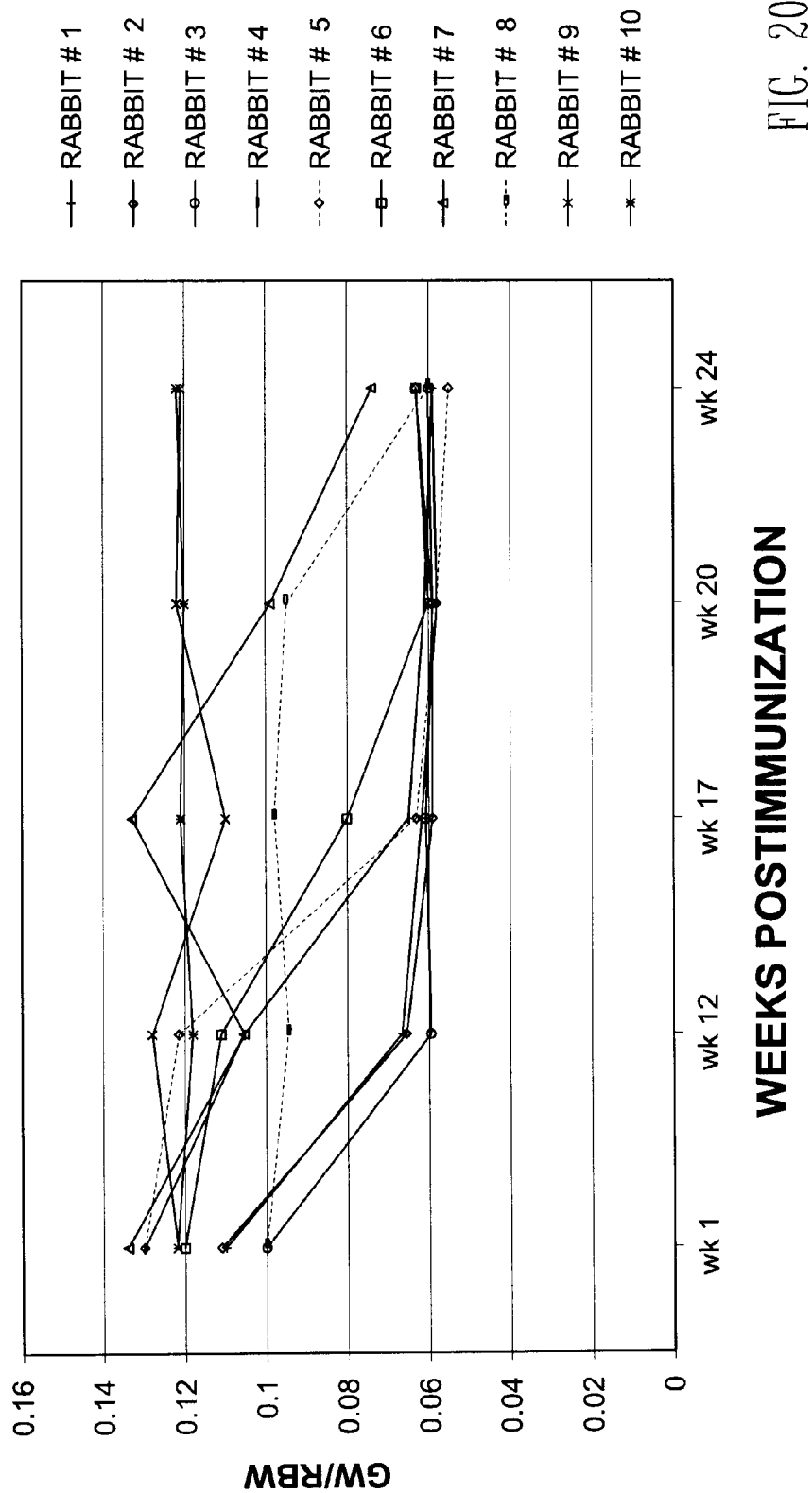
Figure 21:
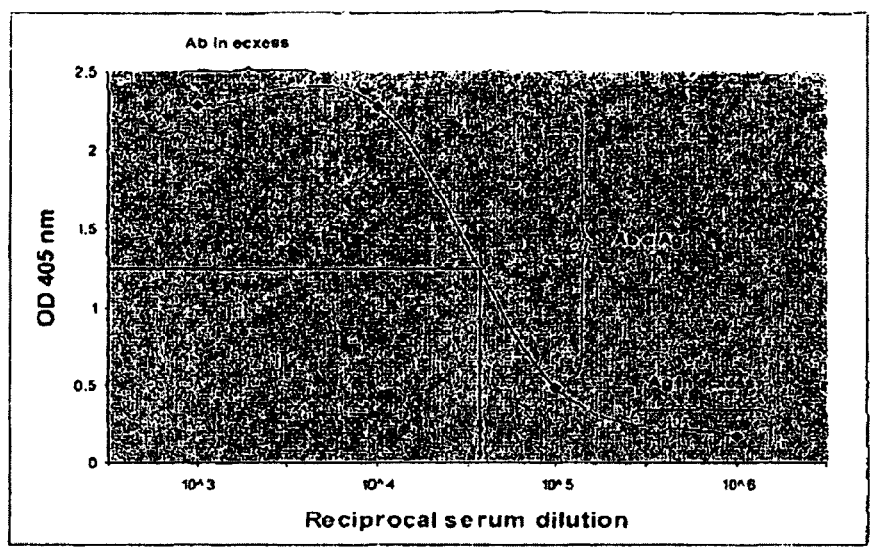

Sera from immunized rabbits were tested for STa-serum neutralization capacity as described under the methods section. Tested sera from three rabbits showed a positive neutralization capacity in suckling mouse assay (gut weight to body weight ratio=0.06±0.001) (FIG. 18) and up to $3 \times 10^4$ mouse units of STa could be completely neutralized by one ml of serum (FIG. 19). Neutralizing antibodies were first detected among these rabbits after 12 weeks post-immunization (fourth immunization). These three rabbits were grouped retrospectively as "group 1" based on the onset of the detectable neutralizing ST-antibody titers. At week 17, post-immunization, another three rabbits had a detectable neutralization titer. These rabbits were grouped as "group 2". At week twenty-four, two more rabbits had mild neutralization capacity against *E. coli* STa. These rabbits were grouped as "group 3". FIG. 20 shows *E. coli* STa-specific serum antibody neutralization bioassay from all rabbits.

Binding Activity.

Indirect ELISA was used to determine the binding capacity of anti-STa IgG. FIGS. 21 through 29 shows the results of binding data for sera from seven bleedings of all rabbits that were giving antibodies against STa at various serum dilutions (10-3 to 10-6). The 10-4 dilution was recognized as the optimal dilution for screening the tested sera for STa-binding capacity (FIG. 21), the equivalence point of antigen antibody interaction).

Figure 22:
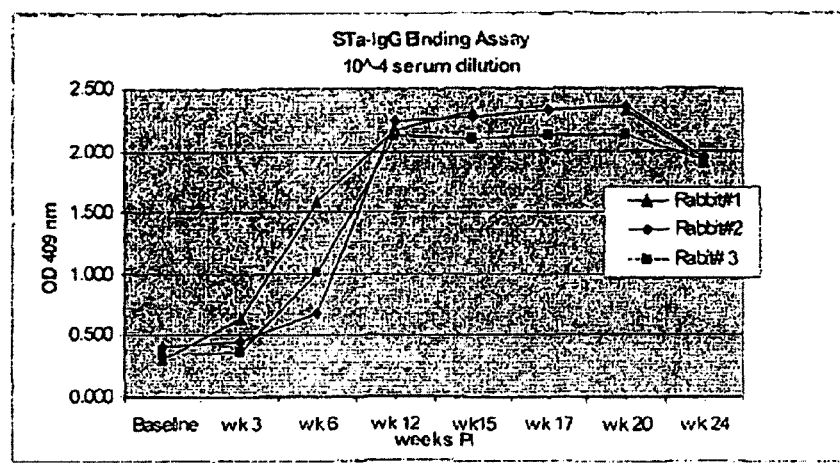
Figure 23:
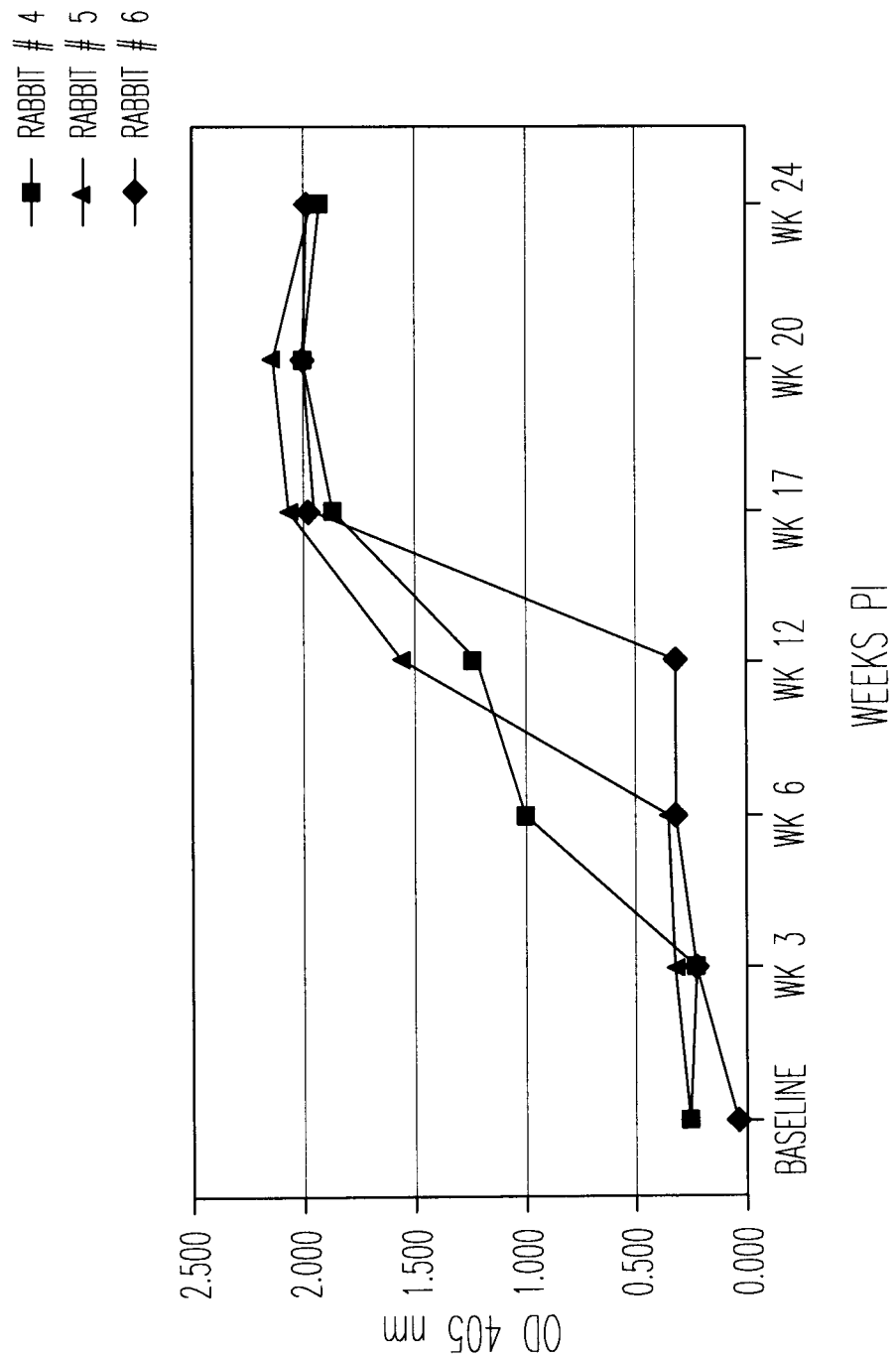
Figure 24:
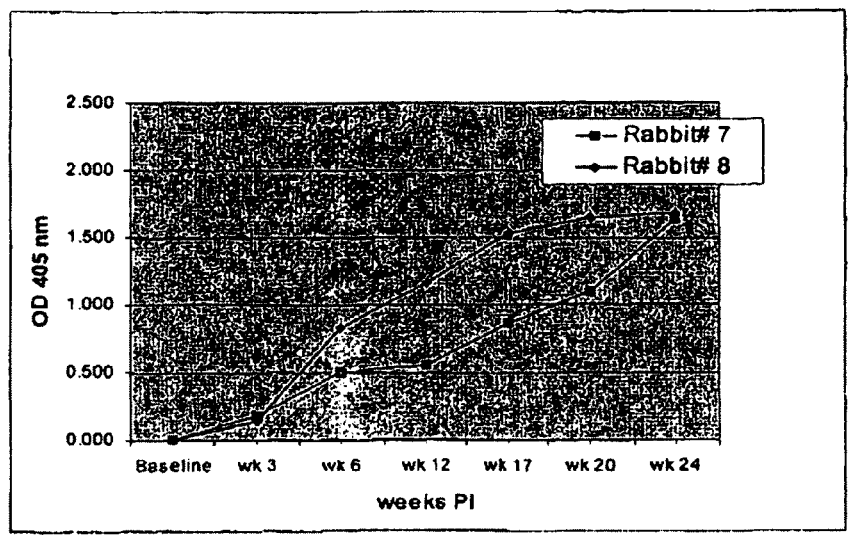
Figure 25:
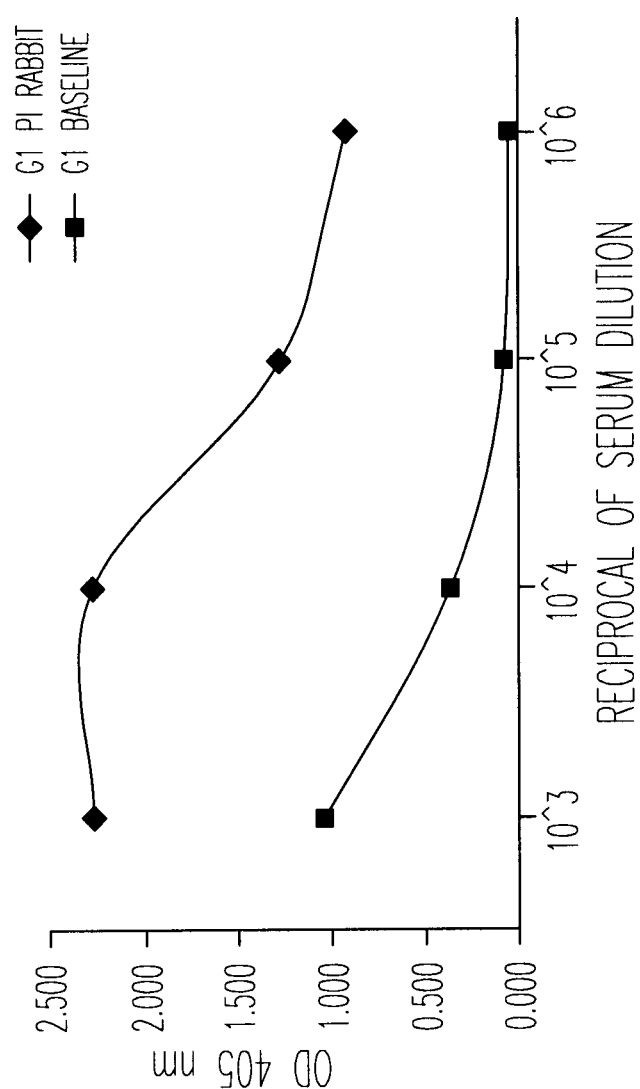
Figure 26:
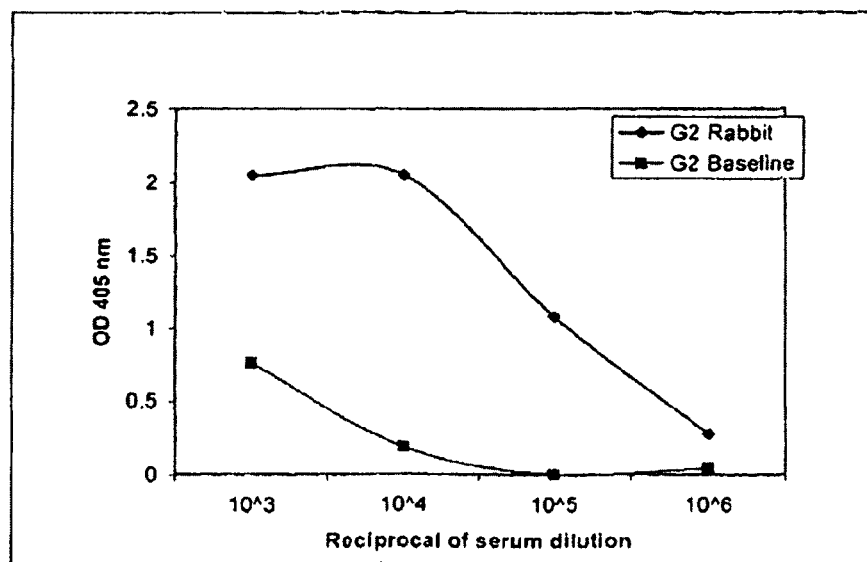
Figure 27:
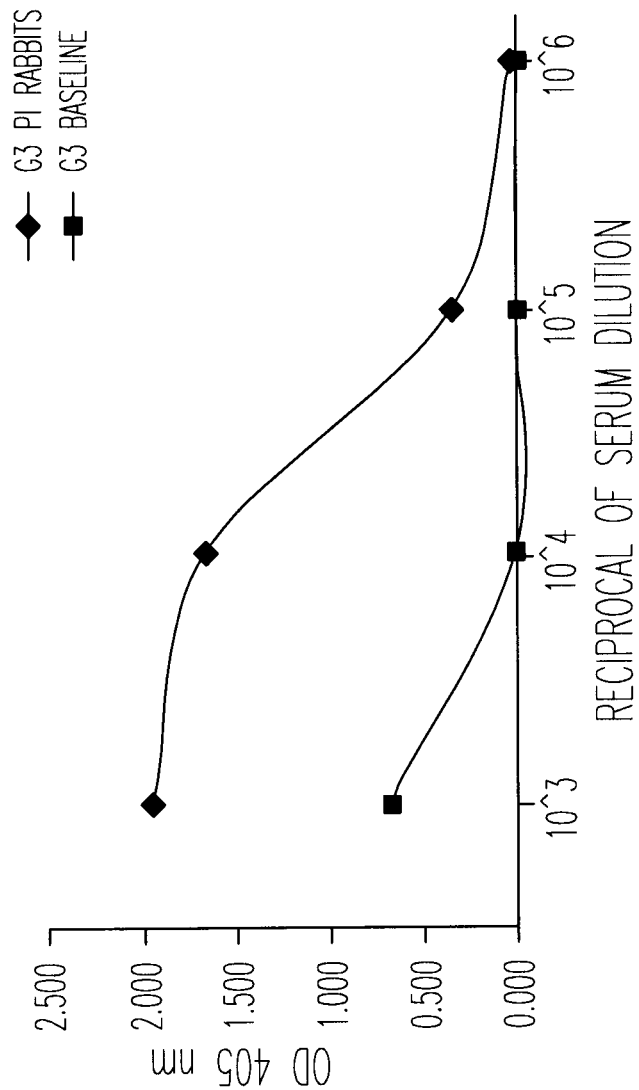
Figure 28:
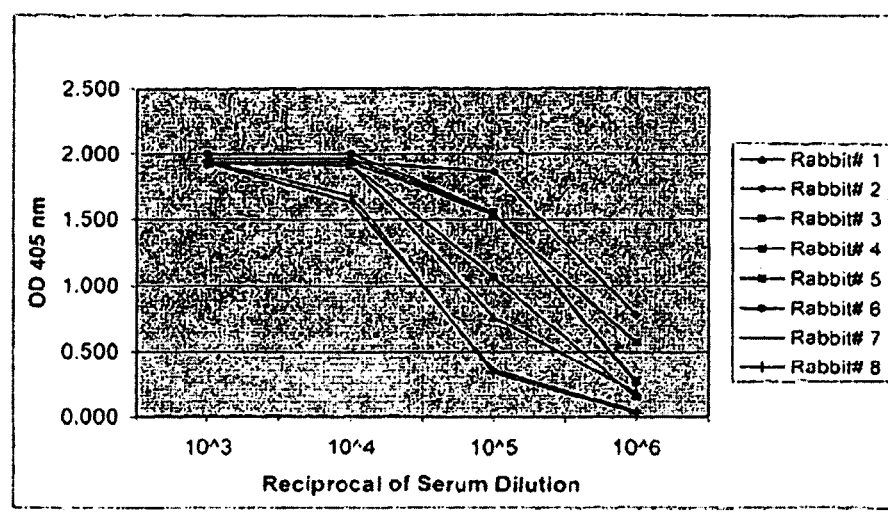
Figure 29:
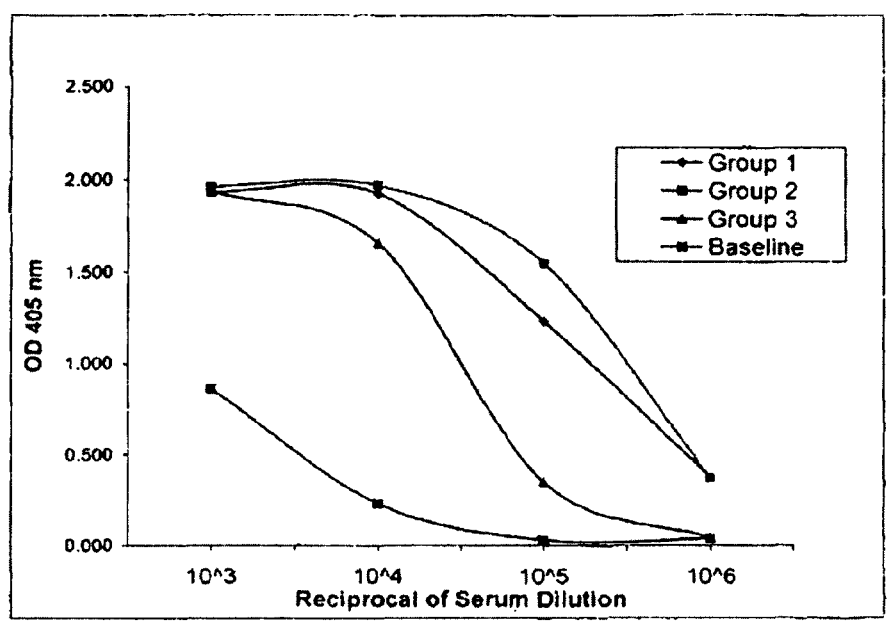

Three weeks after the primary immunization, detectable neutralizing IgG antibodies against STa were not observed. However, based on ELISA assay, slight binding titers were detected. Higher binding antibody titers were only detected 12 weeks post-immunization (FIG. 22). Other three rabbits showed late immune response at week 17 post-immunization (FIG. 23), however higher antibody binding titers (106) and STa-neutralizing antibodies ($3 \times 10^4$ MU/ml serum) were then detected. By 24 weeks post-immunization, other two rabbits mounted mild neutralization and binding titer against *E. coli* STa (FIG. 24). FIGS. 25-29 shows the end titer of *E. coli* STa-specific serum antibody. Mean OD±SD values of STa-specific serum antibody end titer of groups 1, 2 and 3 rabbits after 24-week post-immunization at various serum dilutions are shown in Table XI. Summary of STa-ELISA binding and neutralization end titers of rabbit sera immunized with STasu-BSA conjugate after the primary immunization and during the boosting intervals are presented in Table XII.

STa-Binding Avidity of the Rabbit Immune Sera.

Figure 30:
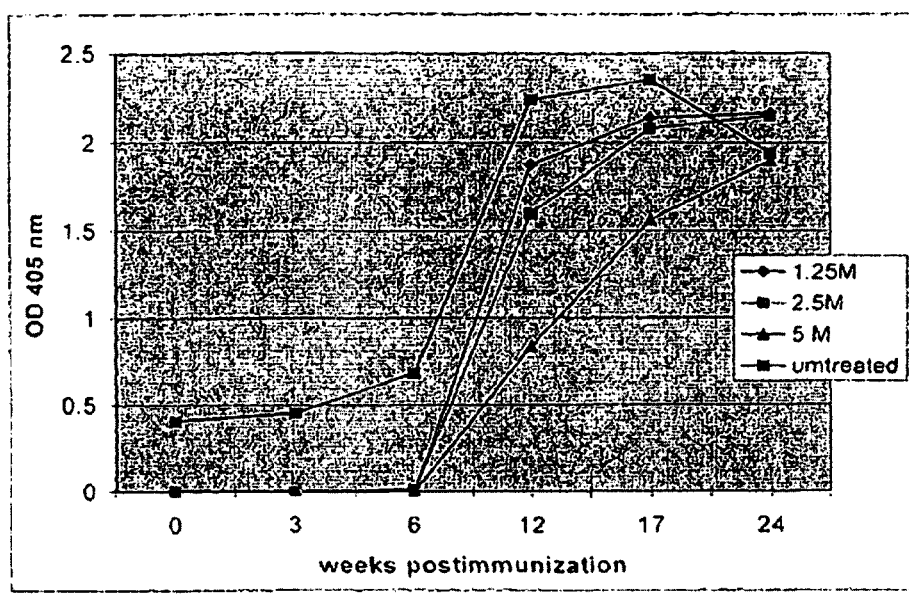
Figure 31:
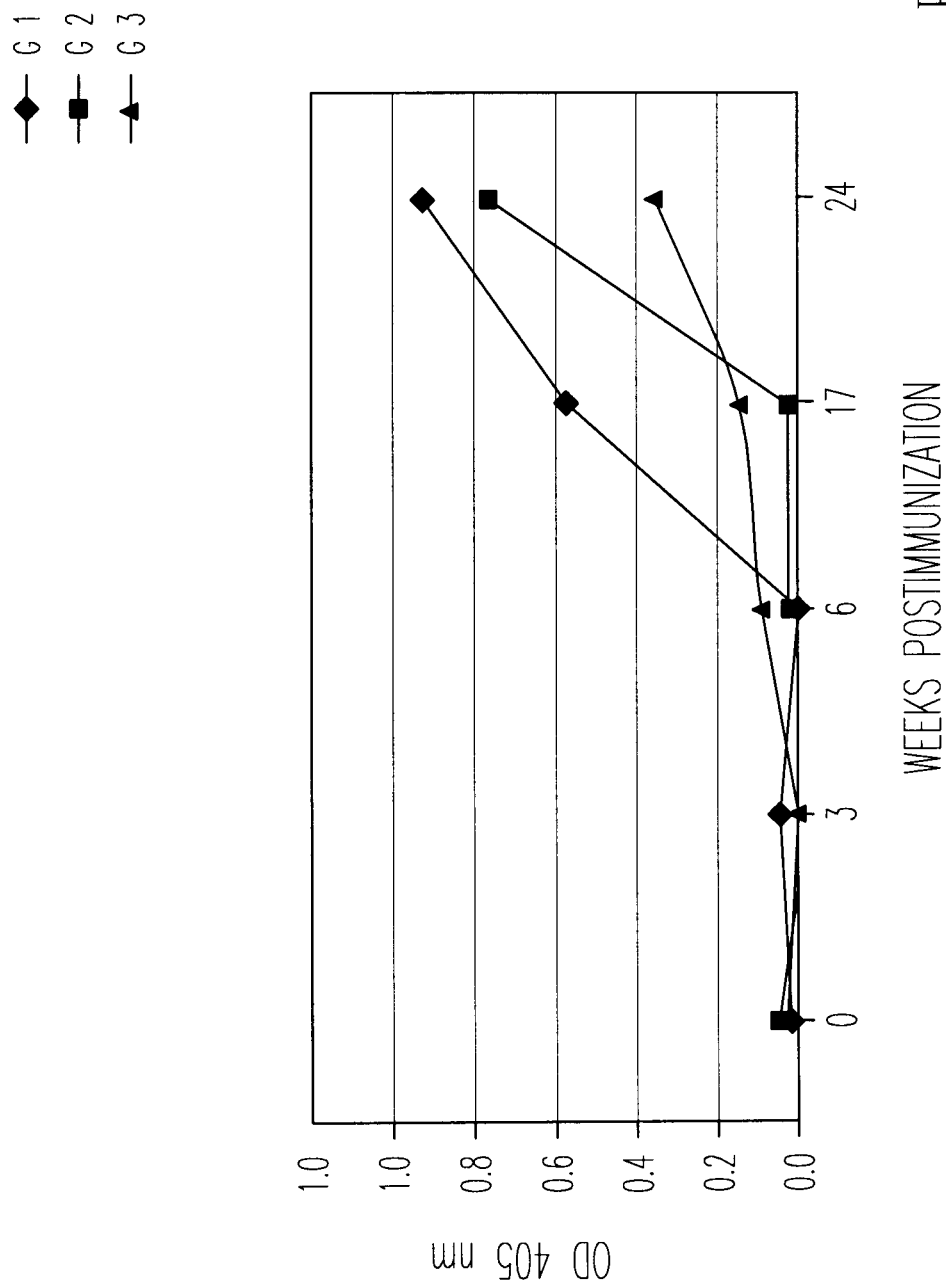
Figure 32:
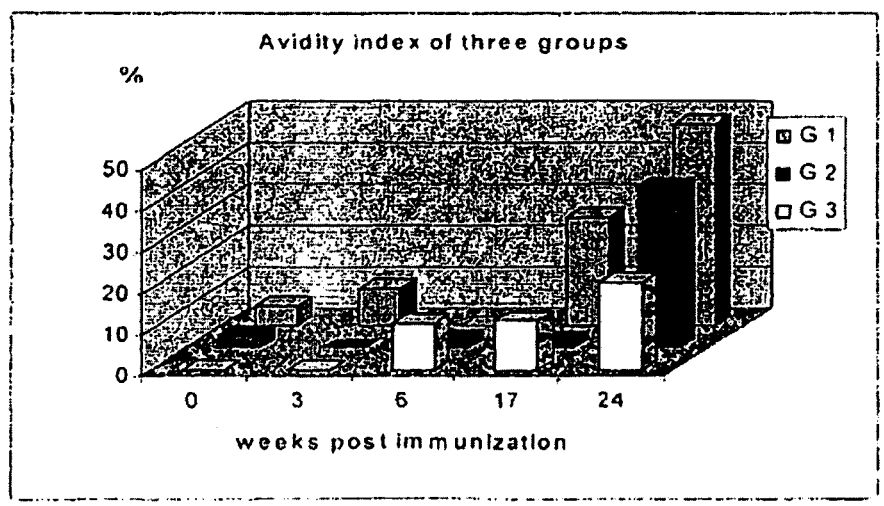

The dissociation effect of ammonium thiocyanate on the STa-binding to its specific antibodies was demonstrated. The dissociation effect of the chaotropic agent on the STa-antibody binding using sera from a rabbit with the highest neutralizing antibody titer is shown in FIG. 30. Sera from other rabbits demonstrated similar avidity patterns. The figure shows the time course evaluation of STa-IgG avidity using ammonium thiocyanate dose response. The increasing molar concentration of ammonium thiocyanate (1.25 M-5 M) needed to dissociate STa-IgG complex is depicted suggesting that the strength of the STa-IgG avidity developed gradually after multiple boosters with the STa-conjugate. A 5 M concentration of the chaotropic agent was determined to be the appropriate cutoff point in order to demonstrate the strength of the avidity of STa-specific serum antibodies. Mean values of the ODs of serum ELISA for the three groups of rabbits assayed using 5 M of the ammonium thiocyanate are depicted in FIG. 31 and summarized in Table XIII. It is noted that there is some variation in the patterns of dissociation of the STa-antibodies from sera of the 3 groups of rabbits, which are largely corresponding to the STa-neutralization and binding titers established for these sera. The avidity index which is calculated by dividing the OD of the sera in the binding ELISA with 5 M of chaotropic agent by the OD of the ELISA binding result for the same sera without treatment with the chaotropic agent (FIG. 32 & Table XIII). By week 24, post-immunization, sera from all three groups of rabbits demonstrated variable avidity indices. It was noted that sera from the first group of rabbits had the highest avidity index, which is associated with the high STa-neutralization and binding titers demonstrated for these sera.

Discussion

Construction of immunogenic ETEC STa has been reported by several investigators who used different chemical coupling protocols to link the STa to carrier proteins as well as the genetic expression of the STa with flagellin as a fusion protein as disclosed in Houghten et al. (1984) *European Journal of Biochemistry* 145, 157-162; Sanchez et al. (1988) *FEBS Letters* 208, 194-198; Clements (1990) *Infection and Immunity* 58, 1159-1166; Klipstein et al. (1983) *The Journal of Infectious Diseases* 147, 318-326; and Pereira et al. (2001) *Microbiology* 147, 861-867, all of which are hereby incorporated by reference. However, limited success in producing high titers STa antisera was reported in those studies. This could be attributed to the uncontrolled cross-linking process of the STa to the carrier proteins which led to the reduction or loss of the STa biological activity as a part of the conjugate as disclosed in Pereira et al. (2001) *Microbiology* 147, 861-867. An important objective of this study was to design and characterize an effective immunogenic STa conjugate usmg the major different peptide-carrier conjugation protocols. Based on the evaluation of four different conjugation procedures, a well-defined STa conjugate with high STa biological activity was produced.

Immunization of ten rabbits with this STa-conjugate led to the production of STa-specific neutralizing antibodies by eight animals. The STa-neutralization and specific binding titers of these sera were higher than those disclosed in Alderete et al. (1978) *Infection and Immunity* 19, 1021-1030; Frantz et al. (1981) *Infection and Immunity* 55, 1077-1084; Lockwood et al. (1984) *Journal of Immunological Methods* 75, 295-307; Löwenadler et al. (1991) *FEMS Microbiology Letters* 82, 271-278; and Pereira et al. (2001) *Microbiology* 147, 861-867, all of which are hereby incorporated by reference. However, some variations in the onset and quality of the immune responses were noticed. Two rabbits demonstrated weaker STa neutralizing titer 20 weeks post-immunization. It is not fully understood why some rabbits differed in their immune response to the STa immunogen. Such individual variations may worth additional investigation in future studies. Comparing data on the STa binding and STa neutralization titers of the sera produced in this study with data from previous reports is presented in Table XIV. Measurement of the avidity of the STa-antibodies using a chaotropic agent, ammonium thiocyanate at several increasing molar concentrations suggested that the avidity of the STa neutralizing antibodies improved throughout the series of boosters administered to the rabbits. Comparison of the avidity of the serum antibodies demonstrated that the strength in the STa antibody avidity developed in time corresponding to the development of the STa-neutralizing and ELISA binding titers of the tested sera. This is consistent with the common knowledge about maturation of antibodies after immunization and continuous boosting protocols as disclosed in Goldblatt, *Encyclopedia of Life Sciences*, John Wiley and Sons, New York (2001), incorporated herein by reference. In summary, we have described the design of a highly defined STa-conjugate and its use in the induction of high STa neutralization and ELISA binding serum titers in immunized rabbits. The carefully designed STa-conjugate and the produced high STa-neutralizing serum antibodies can be evaluated for the design of effective vaccine and/or immunotherapeutic reagents against the STa-producing *E. coli* strains that are associated with a significant proportion of diarrheal disease worldwide.

Example IV

Methods and Materials

Reagents and Instruments.

STa-suBSA conjugates were designed and characterized as described in the previous chapter. All buffers ingredients, Freund's complete and incomplete adjuvant, alkaline phosphatase labeled goat-anti-rabbit IgG antibodies, p-nitrophenyl phosphate, fish gelatin, Tween-20 and ammonium thiocyanate ($NH_4SCN$) were obtained from Sigma Chemical (St. Louis, Mo.). Costar 3590 96-well microtiter plates were obtained from Fisher Scientific (Fairlawn, N.J.). Molecular Devices ThemoMax Microplate reader equipped with SOFT max Pro 2.6.1 was used to read the ELISA plate. A bleeding set (coagulant vacutainer tubes, adaptors and 20 gauge vacutainer needles) was obtained from Becton-Dickinson (BD) (Franklin Lakes, N.J.) and used for rabbit bleeding.

Animals.

Twenty four White leghorn chickens (160-day-old hens) were kept in Michigan State University containment facility for the duration of immunization. Eggs were collected from each bird before primary immunization for baseline.

Immunization Procedure.

Standard operating procedures for handling and immunization of chickens in compliance with the guidelines and recommendations for the Institutional Animal Care and Use Committee (lACUC) of Michigan State University were used. Primary immunization was performed following the subcutaneous route at the neck fold. Each bird received 0.25 mg conjugate protein emulsified in CFA. Immunizations were repeated on days 14 and 28 using Incomplete Freund's adjuvant. Eggs were collected twice/week from each bird. Weekly pools of eggs were processed for IgY extraction from each bird during the immunization protocol for determination of neutralization capacity of the IgY to STa using suckling mouse assay.

STa Neutralization Bioassay.

Figure 33:
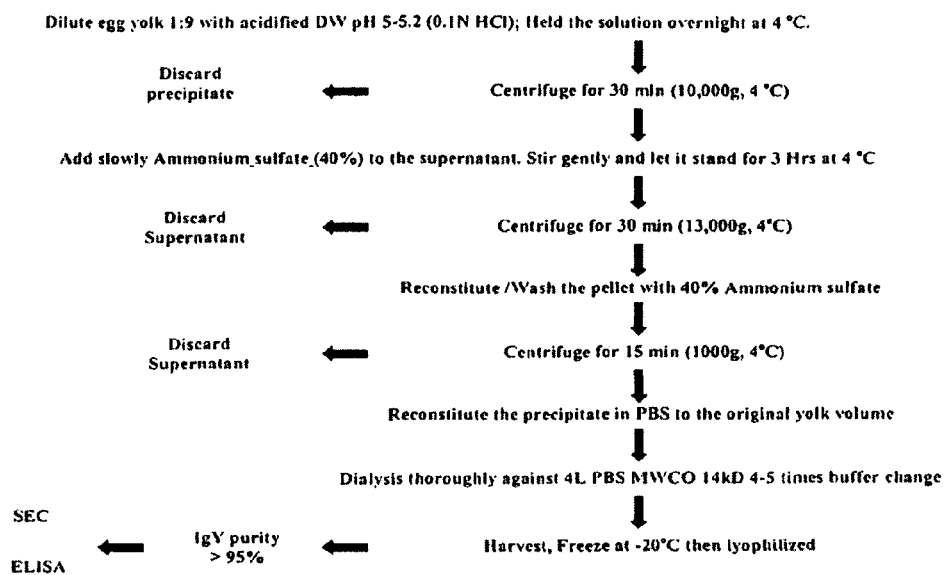

Neutralization activity will be assayed according to Frantz et al., (1987) by incubating dilutions of mammalian antibody (IgG), egg yolk antibody (IgY) and PBS (control) with 25 effective doses (10 ng) of STa at 37° C. for 2 hr in a final volume 100 µl. The contents of each tube were diluted with PBS to 1.0 ml before bioassay. Neutralization titer was expressed as an extrapolated value for the last dilution of IgY that reduce fluid accumulation from the positive control, generally with a gut weight to bodyweight ratio of 0.110 to 0.083. FIG. 33 shows a flow chart for the standardization and optimization of the process of egg yolk antibodies extraction and purification.

Results

Figure 34:
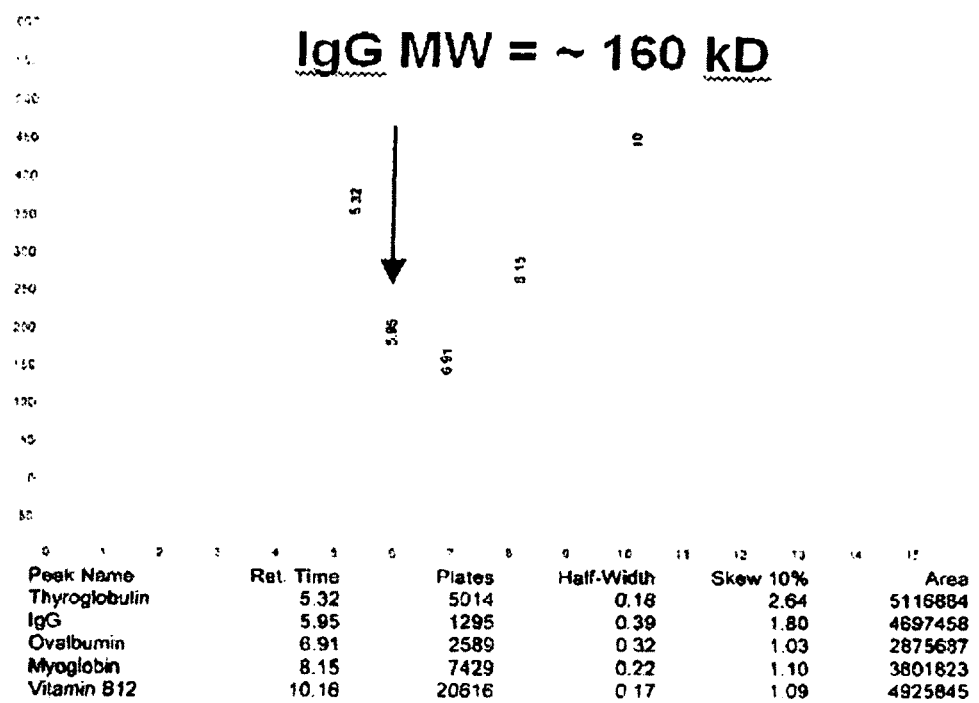
FIG. 34 shows Size Exclusion Chromatography (SEC) of extracted IgY vs standard chromatogram of SEC molecular weight standards.
Figure 35:
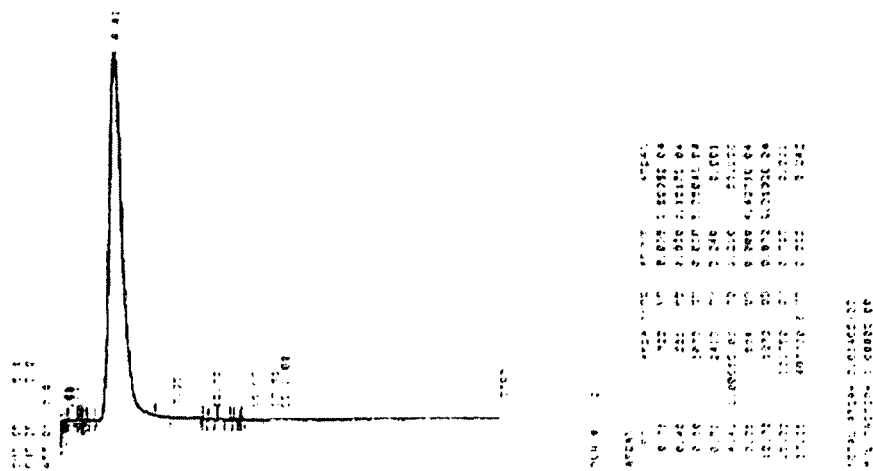
FIG. 35 shows Dose Response Competitive ELISA to establish specificity of the purified IgY from hens before immunization as a baseline.
Figure 36:
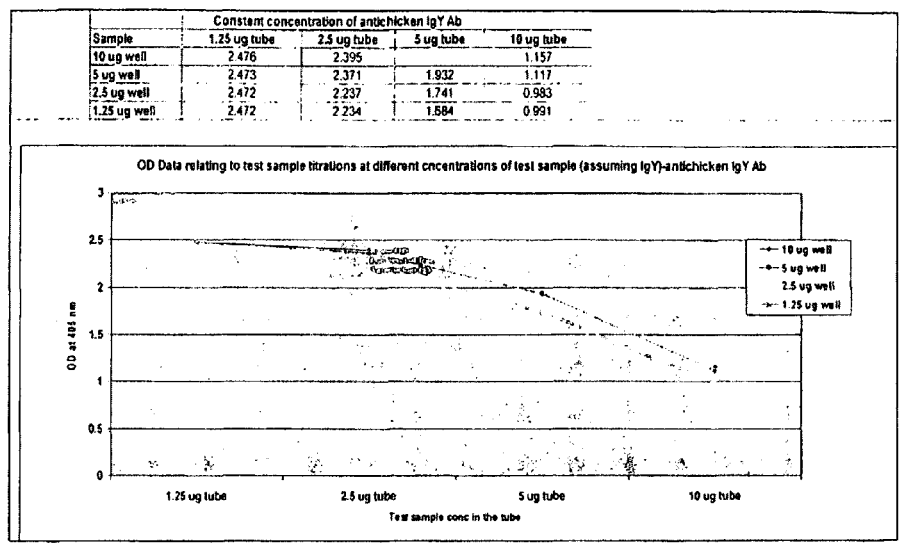
FIG. 36 shows Kinetics of egg yolk-derived STa-neutralizing antibody. Data shows the mean and standard deviation from yolk extract of 6 birds followed over 30 week period after primary immunization followed by boosters. Horizontal red line indicates the cut off for effective STa-neutralization is a gut wt/remaining body wt ratio of 0.083 (Y axis).
Figure 37:
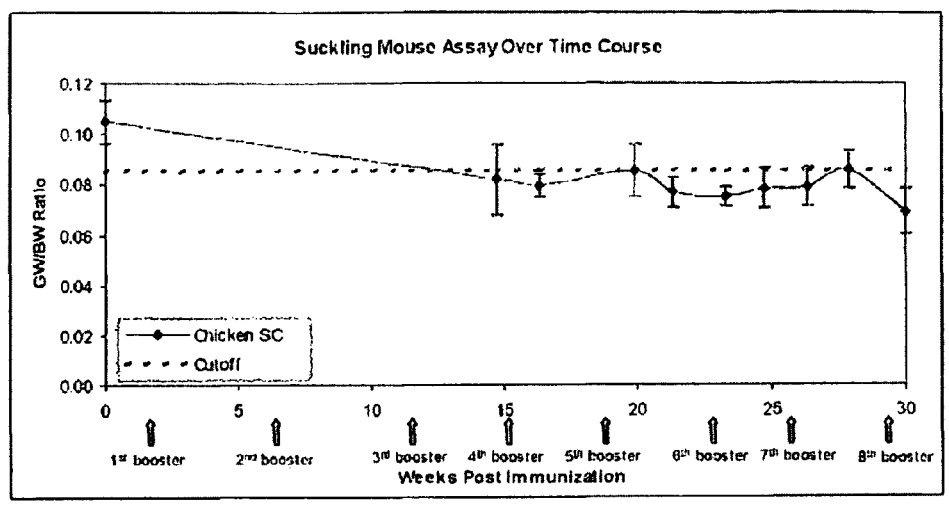
FIG. 37 shows Kinetic of immune response and levels of STa-neutralization measured by suckling mouse assay (Y axis) in 24 hens immunized with the STa vaccine and sampled over 30 weeks period.

Confirmation for the purity and specificity of the produced IGY was demonstrated by: FIG. 34, in which Size Exclusion Chromatography (SEC) of extracted IgY vs standard chromatogram of SEC molecular weight standards are shown. FIG. 35 shows the Dose Response Competitive ELISA to establish specificity of the purified IgY from hens before immunization as a baseline. FIG. 36 shows the kinetics of egg yolk-derived STa-neutralizing antibody. Data shows the mean and standard deviation from yolk extract of 6 birds followed over 30 week period after primary immunization followed by boosters. Horizontal red line indicates the cut off for effective STa-neutralization is a gut wt/remaining body wt ratio of 0.083 (Y axis). Table XV shows the neutralization capacity of STa-specific IgY extracted from egg yolk samples of 24 hens immunized with the STa vaccine. STa neutralization scores based on suckling mouse assay. A ratio of gut weight:remaining body weight of <0.085 signifies a positive STa-neutralization. Avidity index (%) for each sample is listed in the last column. FIG. 37 shows the kinetics of immune response and levels of STa-neutralization measured by suckling mouse assay (Y axis) in 24 hens immunized with the STa vaccine and sampled over 30 weeks period.

CONCLUSION

The use of the ETEC STa vaccine, recently developed by Dr. A. Mandi Saeed of Michigan State University and described under the provisional patent application, for the immunization of egg laying hens resulted in the production of a STa-neutralizing immune response. The ST-a specific antibody levels could be measured after extraction of the antibodies from the yolk of eggs laid by the immunized hens.

The production and demonstration of an effective Immunonoglobulin Y (IgY) with neutralizing capacity to the ETEC STa opens a wide window for prophylactic and therapeutic use of the antibody against ETEC STa-caused diarrheal disease in human and animals. The following is a summary of the proposed embodiments of the produced reagent invention:

A. Prophylactic use:

1. The egg yolk-derived antibody can be enterically coated and administered in appropriate doses to susceptible subjects (infants, adult travelers during the time of highest susceptibility) to offer protection against the STa-diarrhea.

2. This reagent can be commercialized as an additive to infant formula milk in endemic areas to offer protection to infants who are very susceptible to diarrheal disease.

3. The reagent can be similarly added as an additive to milk replacers that are given to new borne calves and piglets to offer protection against calf and piglet scour that is known to have a significant toll on the health and survival of young animals.

B. Therapeutic use: The antibody can also be used immunotherapeutically to treat subjects (humans and animals) suffering from STa-diarrhea. These subjects include human infants and adults and newly borne animals. Of particular importance is the possibility of alleviating the severity of diarrheal disease in subjects that are severely affected such as infants, the elderly, and the immunocompromized subjects.

TABLE I

| Properties | STa = ST1 | STb = STU |
|---|---|---|
| Size | <2 kDa | 5.1 kDa |
| Number of amino acid residues | 18-19 amino acids | 48 amino acids |
| Mechanism of synthesis and secretion | Pre-pro form 72 amino-acid precursor followed by two consecutive peptidase cleavages before extracellular diffusion of 18-19 amino acid mature toxin | 71 amino-acid precursor processed into 48 amino acid mature toxin secreted extracellularly without further processing |
| Number of cysteine residues | Six cysteine residues Three S—S bonds | Four cysteine residues Two S—S bonds |
| Toxic domain | Hydrophobic: 11-14 amino acid especially Ala 13 | Charged amino acids: especially lys-22, lys 23, arg 29 and asp-30 |
| Solubility | Methanol soluble | Methanol insoluble |
| Activity | Active in mice, infant, piglet and calves | Inactive in suckling mice but active in rats and ligated piglet intestinal segment. Have no effect on human small intestine. |
| Trypsin effect | Resistant | Sensitive |
| Mechanism of action | Act on guanylyl cyclase C | Does not act on cyclic nucleotides, Ca, PGE2 and serotonin may be its mode of action |
| Effect on enterocytes: | No effect | Loss of villus epithelial cells and partial villus atrophy (Nagy and Fekete 1999) |
| Prototypes | STaP (protine isolates) and STaH (human isolate) | None |
| Producing strains | ETEC and other bacteria | Only ETEC |

TABLE II

| Toxin and host | No. Amino acids | Sequence | Reference |
|---|---|---|---|
| STaH ETEC | 19 | N-S-S-N-Y-C-C-E-L-C-C-N-P-A-C-T-G-C-Y (SEQ ID NO: 13) | Aimoto et al 1982 |
| STaP ETEC | 18 | N-T-F-Y-C-C-E-L-C-C-N-P-A-C-A-G-C-Y (SEQ ID NO: 12) | Takao et al 1983 |
| STa ETEC (bovine) | 18 | N-T-F-Y-C-C-E-L-C-C-N-P-A-C-A-G-C-Y (SEQ ID NO: 11) | Saeed et al 1984 |

TABLE II-continued

| Toxin and host | No. Amino acids | Sequence | Reference |
|---|---|---|---|
| Citrobacter Freundii | 18 | N-T-F-Y-C-C-E-L-C-C-N-P-A-C-A-G-C-Y (SEQ ID NO: 10) | Guarino et al 1989 |
| Yersinia enterocolitica | 30 | S-S-D-Y-D-C-C-D-Y-C-C-N-P-A-C-A-G-C (SEQ ID NO: 9) | Takao et al 1985 |
| V. cholera Non-O1 | 17 | I-D-C-C-E-I-C-C-N-P-A-C-F-G-C-L-N (SEQ ID NO: 19) | Yoshimura et al 1986 |
| V. cholera non-O1 Hataka | 18 | L-I-D-C-C-E-I-C-C-N-P-A-C-F-G-C-L-N (SEQ ID NO: 18) | Arita et al 1991 |
| V. mimicus | 17 | I-D-C-C-E-I-C-C-N-P-A-C-F-G-C-L-N (SEQ ID NO: 17) | Arita et al 1991 |
| E. coli EAST-1 | 38 | ...A-S-S-Y-A-S-C-I-W-C-T---T-A-C-A-S-C-H-G (SEQ ID NO: 16) | Savarino et al 1993 |
| Conus geographus 13 | 13 | E-C-C-N-P-A-C-G-R-H-Y-S-C (SEQ ID NO: 15) | Gray et al 1981 |
| Guanylin (human) | 15 | P---G-T-C-E-I-C-C-AY-A-A-C-T-G-C (SEQ ID NO: 14) | Greenberg et al 1997 |

TABLE III

| | Primer | Sequence (5-3) | Base pair | Reference |
|---|---|---|---|---|
| (SEQ ID NO: 1) | STa | 5'-TCC GTG AAA CAA CAT GAC GG-3' | 224 | Salvadori et al. 2003 |
| (SEQ ID NO: 2) | | 5'-ATA ACA TCC AGC ACA GGC AG-3' | | |
| (SEQ ID NO: 3) | STl | 5'-TTA ATA GCA CCC GGT ACA AGC AGG-3' | 127 | Olsvick and Strockbine 1993 |
| (SEQ ID NO: 4) | | 5'-CTT GAC TCT TCA AAA GAG AAA ATT AC-3' | | |

TABLE IV

| Step | Temperature (° C.) | Time (min) |
|---|---|---|
| Pre-denature | 95 | 5 |
| Denature | 95 | 1 |
| Annealing | 60 | 1 |
| Extension | 72 | 1 |
| Final extension | 72 | 10 |
| Storage | 4 | 24 hours |

Number of PCR cycles 29 before storage

TABLE V

| Component | Amount/sample (µl) | # of Samples | Amount/two rxns Volume (µl) |
|---|---|---|---|
| 10× buffer A | 2 | 2.5 | 5 |
| dNTP (10 mM) | 0.4 | 2.5 | 1 |
| Sta-F (20 µM) | 0.4 | 2.5 | 1 |
| Sta-R (20 µM) | 0.4 | 2.5 | 1 |
| 25 mM $MgCl_2$ | 0 | 0 | 0 |
| Fisher Taq polymerase | 0.1 | 2.5 | 1 |
| Ultrapure water | 14.7 | 2.5 | 36.75 |
| Total volume | 20 | | 45 |
| Template | 2 | | |

TABLE VI

| | | | |
|---|---|---|---|
| NaCl | 2.52 | $Na_2SO_4$ | 0.14 |
| Na acetate | 10.00 | $MgSO_4$ | 0.05 |
| $K_2HPO_4 \cdot 3H_2O$ | 8.12 | $MnCl_2$ 1% | 0.5 ml |
| Asparagine | 5.00 | $FeCl_3$ 1% | 0.5 ml |

TABLE VII

| Step | Volume ml | Titer | Total $MU/10^7$ | Protein Conc/mg | Sp Ac MU × $10^3$/mg | MED ng | Purification fold |
|---|---|---|---|---|---|---|---|
| Cell Free Filtrate | 30 × $10^3$ | $10^{-2}$ | 3 | 24,660 | 1.22 | 822 | 1 |
| Amberlite XAD-2 BAC | 120 | $10^{-4}$ | 1.2 | 1,378 | 8.70 | 114.9 | 7.13 |

TABLE VII-continued

| Step | Volume ml | Titer | Total MU/10$^7$ | Protein Conc/mg | Sp Ac MU × 10$^3$/mg | MED ng | Purification fold |
|---|---|---|---|---|---|---|---|
| Acetone Fractionation | 60 | 10$^{-5}$ | 6 | 676.8 | 88.7 | 11.28 | 72.67 |
| 60% MCl-gel F | 30 | 10$^{-5}$ | 3 | 267.6 | 112.10 | 8.92 | 91.88 |
| RP-HPLC | 80 | 10$^{-6}$ | 80 | 90.4 | 8849.56 | 0.113 | 7253.28 |

TABLE VIII

| | SuBSA/DMF Method | HSBSA/PB Method | SuBSA/Imidazole Method | Conventional Method |
|---|---|---|---|---|
| Carrier | suBSA | HS-BSA | suBSA | SuBSA |
| Cross linker | Organic soluble carbodiimide (DCC) | Water soluble carbodiimide (EDAC) | Water soluble carbodiimide (EDAC) | Water soluble carbodiimide (EDAC) |
| Medium | N.N. DMF | 5 mM PB (Na2HPO4/NaH2PO4) | Imidazole | 0.1M MES |
| pH | 7-9 | 7 | 7.2 | 5 |
| Stating reactants | 10 mg STa + 14 mg suBSA + 6.5 mg p-NP | 5 mg STa + 12 mg HS-BSA | 10 mg STa + 3.3 mg suBSA | 2 mg STa + 2 mg suBSA |
| Total STa MU | 10 × 10$^6$ | 48 × 10$^4$ | 4 × 10$^6$ | 3 × 10$^3$ |
| Protein Assay | 1.96 mg/ml | 0.277 mg/ml | 1.8 mg/ml | 1.2 mg/ml |
| Conjugation ratio | 4-5:1 | 4:1 | — | — |
| Conjugation efficiency (Lowery protein) | ~52-64% | ~26% | ~40.6% | ~30% |
| Conjugation efficiency (retained biological activity) | 100% | ~20% | 40% | 30% |
| Reference | Atassi et al 1981 | Fuentes et al 2005 | Dean et al. 1990 | Uptima, 2007 |

TABLE IX

| Serial # | Name | RT | Amount pmole |
|---|---|---|---|
| 1 | Gln | 1.78 | 5.983 |
| 2 | Glu | 20.63 | 549.781 |
| 3 | Ser | 25.61 | 147.557 |
| 4 | Gly | 27.42 | 329.482 |
| 5 | His | 29.29 | 174.214 |
| 6 | Thr | 30.47 | 311.339 |
| 7 | Arg | 31.57 | 219.833 |
| 8 | Ala | 31.886 | 507.974 |
| 9 | Pro | 33.18 | 377.778 |
| 10 | Tyr | 37.09 | 499.248 |
| 11 | Cys | 37.53 | 509.796 |
| 12 | Val | 37.85 | 297.137 |
| 13 | Meth | 39.214 | 38.214 |
| 14 | Ile | 43.65 | 118.619 |
| 15 | Leu | 44.80 | 576.721 |
| 16 | Lys | 46.87 | 333.965 |
| 17 | Phe | 38.22 | 386.2 |
| 18 | | | |

TABLE X

| Residue | Total # of residue in STa-suBSA conjugate sample | # of residue/ one BSA molecule | # of residue/ one STa molecule | Conjugation Ratio |
|---|---|---|---|---|
| Threonine | 311.339/8.00 = 38.9 | 34 residues | 1 | 38.9-34 = 4-5 |
| Cysteine | 509.796/8.00 = 63.6 | 35 residues | 6 | 63.6-35 = 28.6/6 = 4-5 |
| Leucine | 576.721/8.00 = 72 | 65 residues | 1 | 72-65 = 7 |
| Alanine | 507.974/8.00 = 63.5 | 48 residues | 2 | 63.5-48 = 15.5/2 = 7-8 |

TABLE XI

| Group | serum dilution | | | |
|---|---|---|---|---|
| | 10$^{-3}$ | 10$^{-4}$ | 10$^{-5}$ | 10$^{-6}$ |
| G1 | 1.933 ± 0.013 | 1.923 ± 0.014 | 1.237 ± 0.568 | 0.379 ± 0.352 |
| G2 | 1.964 ± 0.035 | 1.969 ± 0.031 | 1.550 ± 0.010 | 0.374 ± 0.173 |
| G3 | 1.936 ± 0.006 | 1.656 ± 0.035 | 0.354 ± 0.015 | 0.040 ± 0.010 |
| Baseline | 0.864 ± 0.318 | 0.232 ± 0.155 | 0.033 ± 0.048 | 0.039 ± 0.060 |

TABLE XII

| | Anti-STa Response | | | |
|---|---|---|---|---|
| Bleeding | ELISA Titer | Neutralized STa MU/ml serum (Titer) | Protein Assay mg/ml | Neutralization Specific Activity |
| Baseline | 0 | 0 | 64.5 | — |
| Week 3 PI | 0 | 0 | 66.8 | — |
| Week 6 PI | 0 | 0 | 65.7 | — |
| Week 12 PI | 10,000 | 2000 | 83.5 | 23.95 |
| Week 15 PI | 100,000 | 15,000 | 69.6 | 215.52 |
| Week 20 PI | 1,000,000 | 20,000 | 65.00 | 307.69 |

TABLE XII-continued

Anti-STa Response

| Bleeding | ELISA Titer | Neutralized STa MU/ml serum (Titer) | Protein Assay mg/ml | Neutralization Specific Activity |
|---|---|---|---|---|
| Week 24 PI | 1,000,000 | 20,000 | 65.00 | 307.69 |
| Week 28 PI | 1,000,000 | 30,000 | 65.00 | 461.54 |

TABLE XIII

| | Baseline | Week 3 | Week 6 | Week 12/17 | Week 24 |
|---|---|---|---|---|---|
| | Avidity Index (AI) % after measurement OD at 405 nm | | | | |
| Group 1 | 0.017 (4.70%) | 0.043 (8.91%) | 0.001 (0.03%) | 0.578 (25.94%) | 0.927 (48.21%) |
| Group 2 | 0.043 (3%) | 0 (0%) | 0.022 (2.24%) | 0.027 (1.53%) | 0.762 (38.71%) |
| Group 3 | 0.04 (0%) | 0 (0%) | 0.095 (11.36%) | 0.151 (12.05%) | 0.352 (21.30%) |

TABLE XIV

| References | Maximum neutralization titer | Amount of SMU | Neutralization capacity Total MU/ml serum |
|---|---|---|---|
| Lowenadler et al. 1991 | 1:55 | 30 | 1665 |
| Lockwood and Robertson 1984 | 1:100 | 8 | 800 |
| Frantz and Robertson 1981 | 1:5000 to 1:10,000 | 1 | 5000 to 10,000 |
| Alderete and Robertson 1978 | 1:2,500 | 1 | 2,500 |
| Pereira et al. 2001 | 1:50 for immunogene using native STa fusion protein | 1 | 50 |
| | 1:4000 using mutated STa fusion protein | 1 | 4,000 |
| This study | 1:30,000 | 1 | 30,000 |

TABLE XV

| Bird. No. | STa neutralization G. weight/remaining B. Weight | Neutralization Score | Avidity Index (%) |
|---|---|---|---|
| 1 | 0.073 | ++ | 76.44 |
| 2 | 0.078 | + | 66.70 |
| 3 | 0.056 | ++++ | 91.24 |
| 4 | 0.065 | +++ | 85.58 |
| 5 | 0.066 | +++ | 79.59 |
| 6 | 0.064 | +++ | 52.79 |
| 7 | 0.061 | +++ | 96.46 |
| 8 | 0.068 | +++ | 93.60 |
| 9 | 0.055 | +++ | 59.60 |
| 10 | 0.073 | ++ | 82.28 |
| 11 | 0.073 | ++ | 54.72 |
| 12 | 0.072 | ++ | 86.16 |
| 13 | 0.066 | +++ | 106.17 |
| 14 | 0.066 | +++ | 48.74 |
| 15 | 0.076 | ++ | 87.35 |
| 16 | 0.063 | +++ | 76.83 |
| 17 | 0.070 | +++ | 69.35 |
| 18 | 0.067 | +++ | 88.23 |
| 19 | 0.077 | ++ | 71.59 |
| 20 | 0.082 | + | 80.42 |
| 21 | 0.073 | ++ | 74.89 |
| 22 | 0.083 | -/+ | 70.72 |
| 23 | 0.085 | -/+ | 85.34 |
| 24 | 0.081 | + | 69.84 |

I claim:

1. A vaccine comprising an immunogenic conjugate that comprises heat-stable enterotoxin (STa) protein from *Escherichia coli* comprising an amino terminus that is covalently attached to a carrier protein via a carrier protein succinylated group selected from the group consisting of succinylated a lysine group, and a succinylated N-terminal amino group, wherein the vaccine conjugation efficiency is at least 52% and/or the retained biological activity is 100%.

2. The vaccine of claim 1, wherein said carrier protein is bovine serum albumin.

3. The vaccine of claim 2, wherein the ratio of enterotoxin molecules to one molecule of bovine serum albumin is between 1 and 10.

4. The vaccine of claim 1, wherein said vaccine generates antibody having a specific binding titer of at least $10^{-6}$.

5. The vaccine of claim 1, wherein said enterotoxin protein has a specific activity of at least $1.22\times10^3$ Mouse Unit per milligram (MU/mg).

6. The vaccine of claim 1, wherein said enterotoxin protein has a specific activity of at least $8.70\times10^3$ MU/mg.

7. The vaccine of claim 1, wherein said enterotoxin protein has a specific activity of at least $885\times10^4$ MU/mg.

8. The vaccine of claim 1, wherein said vaccine generates antibody having a neutralization capacity of at least $3\times10^4$ STa mouse units/ml.

9. A method for the prevention of diarrhea or diarrheal related disease or disorder comprising:

a) providing:

i) a subject pregnant with an unborn mammal, ii) the vaccine of claim 1;

b) administering said vaccine to said subject under conditions such that an immune response is generated to enterotoxin, said immune response resulting in antibodies in the colostrum of said pregnant subject.

10. A method for treating subjects at risk for diarrhea or diarrheal related disease or disorder comprising:

a) providing:

i) a subject at risk for diarrhea or diarrheal related disease or disorder, and ii) the vaccine of claim 1;

b) administering said composition to said subject such that said symptoms are reduced.

11. The method of claim 10, wherein the mode of administration for said vaccine is selected from the group consisting of prophylactic, parenteral, intradermal, intramuscular, intraperitoneal, intravenous, subcutaneous, epidural, mucosal, intranasal, rectal, vaginal, sublingual, buccal and oral.

12. The method of claim 10, wherein said diarrhea or diarrheal related disease or disorder is selected from the group consisting of secretory diarrhea, osmotic diarrhea, motility-related diarrhea, inflammatory diarrhea, dysentery, infectious diarrhea, malabsorption disorders, inflammatory bowel syndrome, ischemic bowel disease, bowel cancer, hormone-secreting tumor related disorders, bile-salt diarrhea and chronic ethanol ingestion.

13. The method of claim 10, wherein said subject is a mammal.

14. The method of claim 10, wherein the mode of administering said vaccine is prophylactic.

15. The vaccine of claim 1, wherein said carrier protein is selected from the group consisting of keyhole limpet hemocyanin (KLH), bovine serum albumin (BSA), ovalbumin (OVA), beta-galactosidase (B-GAL), penicillinase, poly-DL-alanyl-poly-L-lysine, and poly-L-lysine.

16. A vaccine comprising an immunogenic conjugate that consists of heat-stable enterotoxin (STa) protein from *Escherichia coli* that is covalently attached to a succinylated carrier protein, wherein the vaccine conjugation efficiency is at least 52% and/or the retained biological activity is 100%.

17. The vaccine of claim 16, wherein said carrier protein is bovine serum albumin.

18. The vaccine of claim 17, wherein the ratio of enterotoxin molecules to one molecule of bovine serum albumin is between 1 and 10.

19. The vaccine of claim 16, wherein said enterotoxin protein has a specific activity of at least $1.22\times10^3$ Mouse Unit per milligram (MU/mg).

20. The vaccine of claim 16, wherein said enterotoxin protein has a specific activity of at least $8.70\times10^3$ MU/mg.

21. The vaccine of claim 16, wherein said enterotoxin protein has a specific activity of at least $885\times10^4$ MU/mg.

22. The vaccine of claim 16, wherein said vaccine generates antibody having a neutralization capacity of at least $3\times10^4$ STa mouse units/ml.

23. The vaccine of claim 16, wherein said vaccine generates an antibody having a specific binding titer of at least $10^{-6}$.

24. A vaccine comprising an immunogenic conjugate that comprises one or more heat-stable enterotoxin (STa) proteins from *Escherichia coli* that are covalently attached to a succinylated carrier protein, wherein the enterotoxin (STa) proteins have a specific activity of at least $885\times10^4$ MU/mg, wherein the vaccine conjugation efficiency is at least 52% and/or the retained biological activity is 100%.

* * * * *

UNITED STATES PATENT AND TRADEMARK OFFICE
CERTIFICATE OF CORRECTION

PATENT NO. : 8,728,478 B2
APPLICATION NO. : 13/054983
DATED : May 20, 2014
INVENTOR(S) : A. Mahdi Saeed It is certified that error appears in the above-identified patent and that said Letters Patent is hereby corrected as shown below:

On the Title Page

On page 2, in column 2, under Item (56) "Other Publications", line 52, delete "Characterizationo f" and insert --Characterization of--, therefor In the Specification In column 1, line 6-9, delete "This invention was made in part with government support under grant number N01-AI-30058, from the National Institutes of Health. As such, the United States government has certain rights to the invention." and insert --This invention was made with government support under AI300581 awarded by the National Institutes of Health. The government has certain rights in the invention.--, therefor In the Claims In column 45, line 42, in Claim 9, after "mammal,", insert --and--, therefor Signed and Sealed this
Fifteenth Day of July, 2014

Michelle K. Lee
*Deputy Director of the United States Patent and Trademark Office*

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 1
tccgtgaaac aacatgacgg                                          20

<210> SEQ ID NO 2
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 2
ataacatcca gcacaggcag                                          20

```
<210> SEQ ID NO 3
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 3
ttaatagcac ccggtacaag cagg                                              24

<210> SEQ ID NO 4
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 4
cttgactctt caaaagagaa aattac                                            26

<210> SEQ ID NO 5
<211> LENGTH: 18
<212> TYPE: PRT
<213> ORGANISM: Artificial Sequence
<220> FEATURE:
<223> OTHER INFORMATION: A synthetic oligopeptide

<400> SEQUENCE: 5

Asn Thr Phe Tyr Cys Cys Glu Leu Cys Cys Asn Pro Ala Cys Ala Gly
 1               5                  10                  15

Cys Tyr

<210> SEQ ID NO 6
<211> LENGTH: 13
<212> TYPE: PRT
<213> ORGANISM: Artificial Sequence
<220> FEATURE:
<223> OTHER INFORMATION: A synthetic oligopeptide

<400> SEQUENCE: 6

Cys Cys Glu Leu Cys Cys Asn Pro Ala Cys Ala Gly Cys
 1               5                  10

<210> SEQ ID NO 7
<211> LENGTH: 18
<212> TYPE: PRT
<213> ORGANISM: Artificial Sequence
<220> FEATURE:
<223> OTHER INFORMATION: A synthetic oligopeptide

<400> SEQUENCE: 7

Asn Thr Phe Tyr Cys Cys Glu Leu Cys Cys Asn Pro Ala Cys Ala Gly
 1               5                  10                  15

Cys Tyr

<210> SEQ ID NO 8
<211> LENGTH: 19
<212> TYPE: PRT
<213> ORGANISM: Artificial Sequence
<220> FEATURE:
<223> OTHER INFORMATION: A synthetic oligopeptide

<400> SEQUENCE: 8

Asn Ser Ser Asn Tyr Cys Cys Glu Leu Cys Cys Asn Pro Ala Cys Thr
 1               5                  10                  15

Gly Cys Tyr
```

```
<210> SEQ ID NO 9
<211> LENGTH: 18
<212> TYPE: PRT
<213> ORGANISM: Artificial Sequence
<220> FEATURE:
<223> OTHER INFORMATION: A synthetic oligopeptide

<400> SEQUENCE: 9

Ser Ser Asp Tyr Asp Cys Cys Asp Tyr Cys Cys Asn Pro Ala Cys Ala
 1               5                  10                  15

Gly Cys

<210> SEQ ID NO 10
<211> LENGTH: 18
<212> TYPE: PRT
<213> ORGANISM: Artificial Sequence
<220> FEATURE:
<223> OTHER INFORMATION: A synthetic oligopeptide

<400> SEQUENCE: 10

Asn Thr Phe Tyr Cys Cys Glu Leu Cys Cys Asn Pro Ala Cys Ala Gly
 1               5                  10                  15

Cys Tyr

<210> SEQ ID NO 11
<211> LENGTH: 18
<212> TYPE: PRT
<213> ORGANISM: Artificial Sequence
<220> FEATURE:
<223> OTHER INFORMATION: A synthetic oligopeptide

<400> SEQUENCE: 11

Asn Thr Phe Tyr Cys Cys Glu Leu Cys Cys Asn Pro Ala Cys Ala Gly
 1               5                  10                  15

Cys Tyr

<210> SEQ ID NO 12
<211> LENGTH: 18
<212> TYPE: PRT
<213> ORGANISM: Artificial Sequence
<220> FEATURE:
<223> OTHER INFORMATION: A synthetic oligopeptide

<400> SEQUENCE: 12

Asn Thr Phe Tyr Cys Cys Glu Leu Cys Cys Asn Pro Ala Cys Ala Gly
 1               5                  10                  15

Cys Tyr

<210> SEQ ID NO 13
<211> LENGTH: 19
<212> TYPE: PRT
<213> ORGANISM: Artificial Sequence
<220> FEATURE:
<223> OTHER INFORMATION: A synthetic oligopeptide

<400> SEQUENCE: 13

Asn Ser Ser Asn Tyr Cys Cys Glu Leu Cys Cys Asn Pro Ala Cys Thr
 1               5                  10                  15

Gly Cys Tyr

<210> SEQ ID NO 14
<211> LENGTH: 16
<212> TYPE: PRT
<213> ORGANISM: Artificial Sequence
```

```
<220> FEATURE:
<223> OTHER INFORMATION: A synthetic oligopeptide

<400> SEQUENCE: 14

Pro Gly Thr Cys Glu Ile Cys Cys Ala Tyr Ala Ala Cys Thr Gly Cys
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: A synthetic oligopeptide

<400> SEQUENCE: 15

Glu Cys Cys Asn Pro Ala Cys Gly Arg His Tyr Ser Cys
1               5                   10

<210> SEQ ID NO 16
<211> LENGTH: 19
<212> TYPE: PRT
<213> ORGANISM: Artificial Sequence
<220> FEATURE:
<223> OTHER INFORMATION: A synthetic oligopeptide

<400> SEQUENCE: 16

Ala Ser Ser Tyr Ala Ser Cys Ile Trp Cys Thr Thr Ala Cys Ala Ser
1               5                   10                  15

Cys His Gly

<210> SEQ ID NO 17
<211> LENGTH: 17
<212> TYPE: PRT
<213> ORGANISM: Artificial Sequence
<220> FEATURE:
<223> OTHER INFORMATION: A synthetic oligopeptide

<400> SEQUENCE: 17

Ile Asp Gly Gly Glu Ile Cys Cys Asn Pro Ala Cys Thr Gly Cys Leu
1               5                   10                  15

Asn

<210> SEQ ID NO 18
<211> LENGTH: 18
<212> TYPE: PRT
<213> ORGANISM: Artificial Sequence
<220> FEATURE:
<223> OTHER INFORMATION: A synthetic oligopeptide

<400> SEQUENCE: 18

Leu Ile Asp Cys Cys Glu Ile Cys Cys Asn Pro Ala Cys Phe Gly Cys
1               5                   10                  15

Leu Asn

<210> SEQ ID NO 19
<211> LENGTH: 17
<212> TYPE: PRT
<213> ORGANISM: Artificial Sequence
<220> FEATURE:
<223> OTHER INFORMATION: A synthetic oligopeptide

<400> SEQUENCE: 19

Ile Asp Cys Cys Glu Ile Cys Cys Asn Pro Ala Cys Phe Gly Cys Leu
1               5                   10                  15

Asn
```

-continued

```
<210> SEQ ID NO 20
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 20
cttgactctt caaaagagaa aatt                                            24
```